United States Patent
Grossman et al.

(10) Patent No.: US 11,020,278 B2
(45) Date of Patent: Jun. 1, 2021

(54) ANTIMICROBIAL COATINGS FOR MEDICAL DRESSINGS AND DRY ANTIMICROBIAL MEDICAL DRESSINGS THEREFROM

(71) Applicant: Allied Bioscience, Inc., Dallas, TX (US)

(72) Inventors: Craig Grossman, Point Roberts, WA (US); Gavri Grossman, Point Roberts, WA (US); Daniel Moros, New York, NY (US); Misagh Alipour, Surrey (CA); Jie Fang, Delta (CA)

(73) Assignee: ALLIED BIOSCIENCE, INC., Plano, TX (US)

( * ) Notice: Subject to any disclaimer, the term of this patent is extended or adjusted under 35 U.S.C. 154(b) by 351 days.

(21) Appl. No.: 15/938,314

(22) Filed: Mar. 28, 2018

(65) Prior Publication Data

US 2018/0280201 A1    Oct. 4, 2018

Related U.S. Application Data

(60) Provisional application No. 62/477,881, filed on Mar. 28, 2017.

(51) Int. Cl.
  *A61F 13/00*     (2006.01)
  *A61K 31/695*    (2006.01)
  *A61F 13/84*     (2006.01)

(52) U.S. Cl.
  CPC .... *A61F 13/00063* (2013.01); *A61F 13/8405* (2013.01); *A61K 31/695* (2013.01); *A61F 2013/8414* (2013.01)

(58) Field of Classification Search
  CPC ... A61K 31/695; C09D 183/04; C09D 183/06
  See application file for complete search history.

(56) References Cited

U.S. PATENT DOCUMENTS

| | | | |
|---|---|---|---|
| 9,528,009 B2 | 12/2016 | Grossman et al. | |
| 9,550,689 B2 | 1/2017 | Grossman | |
| 9,757,769 B2 | 9/2017 | Grossman et al. | |
| 9,849,207 B2 | 12/2017 | Grossman | |
| 9,855,584 B2 | 1/2018 | Grossman et al. | |
| 9,856,360 B2 | 1/2018 | Moros et al. | |
| 9,918,475 B2 | 3/2018 | Moros et al. | |
| 2003/0118631 A1 | 6/2003 | Xing et al. | |
| 2007/0276308 A1 | 11/2007 | Huey et al. | |
| 2009/0155327 A1 | 6/2009 | Martin et al. | |
| 2012/0259302 A1* | 10/2012 | Chaisumdet | A61F 13/36 604/367 |
| 2016/0122587 A1* | 5/2016 | Moros | C09D 183/16 524/588 |

FOREIGN PATENT DOCUMENTS

WO    2016073634 A1    5/2016

OTHER PUBLICATIONS

International Search Report and Written Opinion of the International Searching Authority dated Jun. 1, 2018, in PCT Application No. PCT/US2018/24654.

* cited by examiner

*Primary Examiner* — Kortney L. Klinkel
(74) *Attorney, Agent, or Firm* — Snell & Wilmer L.L.P.

(57) ABSTRACT

Antimicrobial coating compositions are used to form dried residual antimicrobial coatings on medical dressings including gauze, bandages, gowns and dry wipers. Antimicrobial coating compositions comprise at least one of an organosilane $(R^1O)_3Si—R^2—Z$, an organic amine $R^9R^{10}R^{11}N$ a titanium (IV) species, a 1,2-diol, an α-hydroxy acid, a β-hydroxy acid, and an organosilane grafted parylene polymer, wherein $R^1$ is H, alkyl, substituted alkyl, aryl or substituted aryl, $R^2$ is a bivalent linker, Z is a nucleophile, leaving group, or quaternary nitrogen substituent and $R^9$, $R^{10}$, and $R^{11}$ are independently H, alkyl, substituted alkyl, aryl, substituted aryl or cyclic.

8 Claims, No Drawings

ANTIMICROBIAL COATINGS FOR MEDICAL DRESSINGS AND DRY ANTIMICROBIAL MEDICAL DRESSINGS THEREFROM

CROSS-REFERENCE TO RELATED APPLICATIONS

This application claims priority to and the benefit of U.S. Provisional Patent Application Ser. No. 62/477,881 filed Mar. 28, 2017 and entitled "Dry Non-Leaching Antimicrobial Coatings for Medical Dressings," the disclosure of which is incorporated herein by reference in its entirety.

FIELD

The present disclosure relates to medical dressings such as bandages, gauze and wraps. In particular, the disclosure relates to dry antimicrobial coatings for medical dressings such as gauze.

BACKGROUND

Infection resistant medical dressings have the potential to minimize risk of hospital acquired infections in a wound prior to release of the patient from the hospital. Further, antimicrobial wound dressings in general may provide for improved healing of wounds, such as quicker healing and less scarring due to the elimination of infections in the wound and reduction of the re-shedding of microbes back into the wound from the dressing. In the medical setting, antimicrobial textiles (e.g., a dry critical wiper) would also benefit from having infection resistant coatings, such as to prevent transfer of organisms from a site in the treatment room to the wound site on a patient.

Antimicrobial compositions that may be applied to bandages, or applied directly to a wound, are known. However, the majority of these compositions are oily and messy to use, especially by a consumer at home that may be less skilled in applying such compositions than a trained practitioner at a clinic. For example, an antibacterial ointment applied to areas adjacent to the actual wound site may prevent the adhesive on a bandage from adhering properly and completely to the skin.

Antimicrobial bandages and dressings are known. However, many of these bandages and dressings do not exhibit broad spectrum antimicrobial efficacy and some have messy oily coatings. For example, QuickMed Technologies ("QMT") provides an antimicrobial gauze bandage coated with poly(diallyl dimethyl ammonium chloride), (abbreviated as polyDADMAC). Although this gauze shows efficacy against *Staph.*, *E. coli*, and other bacteria (including some antibiotic resistant strains), there is no report of virucidal efficacy, or any efficacy against yeasts, molds and spores. Other medical dressings comprise compositions based on silver or nickel oxide, neither of which is capable of providing virucidal efficacy. Another commercially available product is Kerlix™ AMD Antimicrobial Gauze Bandage Rolls by Medtronic, which is based on polyhexamethylene biguanide (PHMB). This product shows efficacy against many Gram positive and Gram negative bacteria, including various antibiotic resistant bacteria, yeasts and fungi, but does not report efficacy against viruses or spores. Consumer use bandages (Curad®, BandAid®, and various generic bandages) typically comprise the "triple antibiotic" ointment (containing bacitracin zinc, neomycin sulfate and polymyxin B sulfate), which is oily and not effective across a broad spectrum of microorganisms.

Notwithstanding these and other achievements in the field of antimicrobial dressings, new coatings and methods of coating medical dressings are still needed. In particular, new dry coatings that are applicable to all or to at least many types of medical dressings are still needed in both the professional and consumer markets.

SUMMARY

It has now been discovered that certain organosilane compositions are applicable to medical dressings, and find use in providing residual antimicrobial efficacy to various medical dressings such as medical gauze. Residual antimicrobial coatings on medical dressings herein are dry to the touch. Further, residual antimicrobial medical dressings disclosed herein may be sterilized and packaged as sterile without damage to the residual antimicrobial coating. Antimicrobial coatings on medical dressings may be purposely designed to be permanently on the dressing, or dissolving from the dressing, such as needed to fit a particular application.

In various embodiments, antimicrobial coating compositions usable for coating and drying on medical dressings comprise an aqueous solution of at least one organosilane $(R^1O)_3Si$—$R^2$—$Z$, wherein $R^1$ is H, alkyl, substituted alkyl, aryl or substituted aryl, $R^2$ is a bivalent linker, and Z is a nucleophile, leaving group, or quaternary nitrogen substituent.

In various aspects, the medical dressing is selected from the group consisting of adhesive bandages, gauze rolls, gauze pads, wraps, sponge material, breathable films, patient gowns, examination gowns, surgical gowns, and disposable dry wiper substrates.

In various aspects, $R^2$ is —$CH_2CH_2CH_2$—, and Z is —$NH_2$, a halogen, —$N(CH_3)_3{}^+X^-$, or —$N(CH_3)_2(n$-$C_{18}H_{37})^+X^-$, wherein $X^-$ is chloride, bromide, iodide, or bitartrate.

In various embodiments, antimicrobial coating compositions for use in coating medical dressings further comprise at least one amine having structure $R^9R^{10}R^{11}N$ wherein $R^9$, $R^{10}$, and $R^{11}$ are independently H, alkyl, substituted alkyl, aryl, substituted aryl or cyclic. In certain examples, an organic amine comprises diethanolamine or triethanolamine. In certain examples, the antimicrobial coating compositions comprise at least one organosilane and triethanolamine.

In various aspects, Z is halogen and the organic amine is diethanolamine or triethanolamine, or mixtures thereof.

In various embodiments, antimicrobial coating compositions for use in coating medical dressings comprise at least one titanium (IV) species selected from the group consisting of $TiO_2$, $Ti(OR^3)_4$, $Ti$—$(O-i-C_3H_7)_4$, $TiCl_4$ or a mixture of peroxotitanium acid and peroxo-modified anatase sol, wherein each $R^3$ is independently alkyl, substituted alkyl, aryl, or substituted aryl.

In various embodiments, antimicrobial coating compositions for use in coating medical dressings comprise the reaction product between a titanium (IV) oxide of formula $Ti(OR^3)_4$ wherein each $R^3$ is alkyl, substituted alkyl, aryl, or substituted aryl, and a 1,2-diol, α-hydroxy acid, or 3-hydroxy acid.

In various embodiments, a dry medical dressing is disclosed. The dry medical dressing comprises: a nonwoven or woven substrate; and an antimicrobial coating composition dried thereon, the antimicrobial coating composition comprising: (i) at least one organosilane $(R^1O)_3Si—R^2—Z$; and (ii) at least one amine $R^9R^{10}R^{11}N$ wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic, wherein the dry medical dressing exhibits residual antimicrobial efficacy against at least one of *E. coli, S. aureus,* or *S. epidermidis.*

In various aspects, a dry medical dressing substrate has a coating dried thereon consisting essentially of octadecyldimethyl-(3-trimethoxysilylpropyl) ammonium chloride, 3-chloropropyltrimethoxysilane, and triethanolamine.

In various aspects, a dry medical dressing substrate has a coating dried thereon consisting essentially of 3-aminopropyltriethoxysilane and triethanolamine.

In various examples, the medical dressing comprises a substrate selected from cellulose wiper, polyester gauze, or cotton gauze.

In various embodiments of the present disclosure, a method of producing a dry medical dressing that exhibits residual antimicrobial efficacy against at least one of *E. coli, S. aureus,* or *S. epidermidis* is disclosed. The method comprises saturating the medical dressing with an aqueous composition comprising at least one organosilane $(R^1O)_3Si—R^2—Z$ and at least one amine $R^9$, $R^{10}$, and $R^{11}N$; and then drying the medical dressing to produce the dry medical dressing, wherein $R^1$ is H, alkyl, substituted alkyl, aryl or substituted aryl, $R^2$ is a bivalent linker, Z is a nucleophile, leaving group, or quaternary nitrogen substituent, and $R^9$, $R^{10}$, and $R^{11}$ are independently H, alkyl, substituted alkyl, aryl, substituted aryl or cyclic.

In various aspects of the method, the medical dressing is selected from the group consisting of adhesive bandages, gauze rolls, gauze pads, wraps, sponge material, breathable films, patient gowns, examination gowns, surgical gowns, and disposable dry wiper substrates.

In various aspects of the method, $R^2$ is $—CH_2CH_2CH_2—$, and Z is $—NH_2$, a halogen, $—N(CH_3)_3^+X^-$, or $—N(CH_3)_2(n-C_{18}H_{37})^+X^-$, wherein $X^-$ is chloride, bromide, iodide, or bitartrate.

In various aspects, the at least one organosilane consists essentially of octadecyldimethyl-(3-trimethoxysilylpropyl) ammonium chloride, 3-chloropropyltrimethoxysilane, and the at least one amine is triethanolamine.

In various aspects, the at least one organosilane consists essentially of 3-aminopropyltriethoxysilane and the at least one amine is triethanolamine.

In various aspects of the method, curing the aqueous composition on the medical dressing comprises any combination of ambient drying, heating in an autoclave, or annealing at elevated temperatures. In certain examples, the drying of the aqueous composition on the medical dressing comprises ambient, passive drying to provide a medical dressing that is dry to the touch.

In various embodiments, a method of applying an antimicrobial coating composition to a medical dressing comprises any number of textile coating processes such as various roll-to-roll coating methods wherein a sheet of substrate off a roll is immersed in or sprayed with the antimicrobial coating composition. The treated substrate may then be rolled back up and processed at a later time into individual medical dressing articles.

In various embodiments, an antimicrobial coating composition is packaged in an aerosolized or non-aerosol package, and the containerized composition used to spray onto medical dressings before the dressing is placed on a patient, sprayed onto the medical dressing and the skin areas surrounding the dressing after the dressing is placed on the patient.

DETAILED DESCRIPTION

The detailed description of exemplary embodiments makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Antimicrobial coating compositions are disclosed. In various embodiments, antimicrobial coating compositions comprise at least one of an organosilane, a titanium (IV) species, and a parylene polymer, in any combination. Antimicrobial coating compositions provide residual antimicrobial coatings on medical dressings when applied thereon. In various embodiments, coatings are useful on medical dressings that are sterilized and packaged sterile, and are durable for extended periods of time even in continuous contact with wound exudate, various environments conditions, warmth and perspiration. In various embodiments, an antimicrobial coating on a medical dressing is designed to dissolve off over time, such as into a wound area. This is useful, for example, for triage wrapping of a wounded patient in the field where the dissolving coating may mitigate the possibility of infection in a wound area while the patient is being transported to the hospital.

The treatment of medical dressings with a silane species and a mixture of peroxotitanium acid solution and peroxo-modified anatase sol is disclosed in U.S. Pat. No. 9,856,360 and in PCT International Application Serial No. PCT/US2015/059080, the disclosures of which are incorporated herein by reference in their entireties.

As used herein, the term "organosilane" refers to silicon-containing organic chemicals, as opposed to inorganic forms of silicon, such as $SiO_2$ and water glass species ($Na_2SiO_3$, and the like). An organosilane is typically a molecule including carbon and silicon atoms, but may also include any other heteroatoms such as oxygen, nitrogen, or sulfur. Organosilane compounds may be chemical reactive or inert, and may be monomeric, dimeric, trimeric, tetrameric, or polymeric. Organosilane monomers may be chemically reactive in that they at least partially hydrolyze or polymerize, or form various adducts and/or polymers with other chemical species. Exemplary organosilanes include, but are not limited to, to organosilanes having three reactive groups on silicon and one non-hydrolyzable group, such as for example, 3-chloropropyltrialkoxysilane and 3-aminopropyltrialkoxysilane, and adducts, hydrolysis products, self-condensation products, and polymeric reaction products therefrom.

As used herein, the term "titanium (IV) species" refers to any chemical compound comprising at least one tetravalent titanium atom, regardless if monomeric, dimeric, trimeric, or polymeric. Non-limiting examples include titanium (IV) oxide ($TiO_2$) in any form, other Ti(IV) species, (e.g., $TiCl_4$, Ti—$(O-i-C_3H_7)_4$ or any other Ti(IV) alkoxide, phenoxide or halide). Various forms of $TiO_2$ for use herein include, but are not limited to, rutile, anatase, brookite, hollandite-like, ramsdellite-like, $\alpha$-$PbO_2$-like, baddeleyite-like form, orthorhombic $TiO_2$—OI, cubic, and/or cotunnite-like forms. The most common crystalline forms are anatase, brookite and rutile. In various examples, Ti(IV) species for use herein comprise Ti nanoparticles. Further, Ti(IV) species for use herein include "titanyl-oxide moieties," which is a broad term defined herein to include any and all Ti compounds and mixtures known to form $TiO_2$ thin films, or at least suspected as able to form $TiO_2$ thin films, such as via the sol-gel process. A titanyl sol-gel is a precursor in the preparation of $TiO_2$ thin films. For example, a mixture of $Ti(OC_4H_9)_4$, ethanol, water, and diethanolamine, in a 1:26.5:1:1 molar ratio, has been disclosed as forming a $TiO_2$ film (see J. Yu, et al., *Materials Chemistry and Physics*, vol. 69, pp 25-29 (2001)). This reference further discloses that whether or not the film is photocatalytic depends, inter alia, on the curing conditions for the sol-gel after surface application, e.g. using high temperatures. In another non-limiting example, a sol-gel route to mesoporous and nanocrystalline anatase thin layers begins with acidic hydrolysis of titanium isopropoxide, (see F. Bosc, *Chem. Mater.*, 15(12), pp 2463-2468, (2003)).

In certain examples, titanyl-oxide moieties for use herein comprise a colloidal suspension of from about 0.5 wt. % to about 50 wt. % $TiO_2$ in water. In other examples, titanyl-oxide moieties comprise an aqueous mixture of Ti—$(O-i-C_3H_7)_4$ usable to create a thin film of $TiO_2$ via the sol-gel process. Such compositions may also comprise an organic solvent, such as an alcohol like n-propanol or n-butanol, a surfactant, or an acid catalyst. In the sol-gel process, $TiO_2$ is prepared by hydrolysis, condensation and polycondensation of a titanium alkoxide, such as Ti—$(O-i-C_3H_7)_4$ or $TiCl_4$. A $TiO_2$ sol-gel composition, when coated onto a portion of a surface, provides a thin film $TiO_2$ coating on the portion of the surface.

In various embodiments, titanyl-oxide moieties comprise $Ti(OR^3)_4$, wherein $R^3$ is alkyl, substituted alkyl, aryl, or substituted aryl, and wherein the four separate $R^3$ groups are identical or different. Examples of $Ti(OR^3)_4$ include, but are not limited to, titanium tetramethoxide, titanium tetraethoxide, titanium methoxide triethoxide, titanium tetra-n-propoxide, titanium tetra-i-propoxide, and titanium tetraphenoxide. Depending on the physical properties of the titanium (IV) species, the compound may be used neat (e.g. Ti—(O-i-$C_3H_7)_4$) or dissolved in an alcohol or other organic solvent(s), such as the corresponding alcohol, where feasible, (methanol, ethanol, i-propanol, etc.). Thus, titanyl-oxide moieties may in some instances comprise a solution of Ti—$(O-i-C_3H_7)_4$ in isopropanol or some other alcohol.

In various embodiments, titanyl-oxide moieties comprise $Ti(OR^3)_4$, wherein $R^3$ is alkyl, substituted alkyl, aryl, or substituted aryl. In certain aspects, titanyl-oxide moieties may further comprise a solvent selected from the group consisting of water, alkanols, diols, triols, chlorinated organic solvents, ethers, amines, esters, ketones, aldehydes, lactones, phenolics, and mixtures thereof. In certain examples, a solvent is selected from, but not limited to, water, methanol, ethanol, n-propanol, i-propanol, ethylene glycol, 1,2-propanediol, 1,3-propanediol, glycerin, methylene chloride, trichloromethane, carbon tetrachloride, ethylene glycol monoalkyl ether, ethylene glycol dialkylether, propylene glycol monoalkyl ether, propylene glycol dialkyl ether, ethylene glycol monophenyl ether, ethylene glycol diphenyl ether, propylene glycol monophenyl ether, propylene glycol diphenyl ether, diethylether, tetrahydrofuran, pyridine, triethanolamine, diethanolamine, triethylamine, ethylacetate, acetone, furfural, and N-methyl-2-pyrrolidone, and combinations thereof. In various examples, titanyl-oxide moieties consist essentially of Ti—$(O-i-C_3H_7)_4$. Other examples include Ti—$(O-i-C_3H_7)_4$ and an alcohol, and a composition comprising Ti—$(O-i-C_3H_7)_4$ and iso-propanol.

In various examples, titanyl-oxide moieties for use herein comprise an aqueous solution of peroxotitanium acid and peroxo-modified anatase sol, which is disclosed in the literature as a room temperature route to $TiO_2$ thin films, (see Ichinose, H., et al., *Journal of Sol-Gel Science and Technology*, September 2001, Volume 22, Issue 1-2, pp 33-40, and Ichinose, H., et al., *J. Ceramic Soc. Japan*, Volume 104, Issue 8, pp 715-718 (1996)).

In various examples, the titanyl-oxide moieties for use herein is a sol-gel that comprises about 0.5 wt. % peroxotitanium acid and about 0.5 wt. % peroxo-modified anatase sol, remainder water. A non-limiting example of a titanyl-oxide moieties composition for use herein comprises 0.85 wt. % of a mixture of peroxotitanium acid and peroxo-modified anatase sol (titanium oxide (IV)), remainder water. In various examples, a titanyl-oxides moieties composition comprises 0.8-0.9 wt. % of a mixture of titanium oxide (IV) and peroxotitanium acid, with the remainder, i.e., 99.1-99.2 wt. %, water. In various embodiments, this sol-gel mixture may be referred to as "0.85 wt. % aqueous peroxotitanium acid and peroxo-modified anatase sol."

Titanium (IV) species for use in various coating processes may be white or transparent, and may be photocatalytic or not. A titanium (IV) species, including the group of titanyl-oxide moieties discussed above, may be cast onto fiber surfaces to produce an antimicrobial coating or used as a bonding agent to bond other substances, such as organosilanes, to fibers and soft surfaces to form more durable antimicrobial coatings on medical dressings. Further, if the antimicrobial activity of the titanium(IV) species is light-activated, i.e., photocatalytic, the coating may be disposed on a transparent bandage or other dressing such that incident light can pass through the dressing and land on the photocatalyst.

As used herein, the term "adduct" refers to a chemical combination of two or more chemical species, regardless of what forces hold the particular combination together. For example, two chemical species may form an adduct that comprises an ionic or covalent bond between the species, or even van der Waals or hydrogen bonds. A non-limiting example is the adduct $(MeO)_3Si$—$CH_2CH_2CH_2$—$N(CH_2CH_2OH)_3^+Cl^-$ resulting from the reaction, under certain conditions, between 3-chloropropyltrimethoxysilane and triethanolamine. Another non-limiting adduct is the hydrogen bonded chelate resulting from the association between triethanolamine and 3-aminopropyltriethoxysilane, wherein the —OH groups of the triethanolamine are hydrogen bonded to the —$NH_2$ group of the organosilane. Adducts for use in various embodiments do not need to comprise an organosilane, as they may be formed, for example, from the combination of other molecular species. A non-limiting example of such an adduct not comprising silicon is the compound resulting from reaction of a titanium (IV) species such as Ti—(O-i-$C_3H_7$)$_4$ and a diol.

As used herein, the term "polymer" takes on its ordinary meaning, which is at least two monomer species linked together to form any larger molecular weight compound. For the sake of simplicity, a polymer includes at least four monomers so as to distinguish from a dimer, trimer and tetramer. Thus, as few as five monomers covalently linked together comprise a polymer for purposes for use in various embodiments. In accordance with the ordinary meaning, a polymer may include any combination of any monomeric species, and may be linear, branched or other configuration (e.g. dendritic). Further, a polymer may be organized as a homopolymer of one monomer or any type of co-polymer having more than one monomeric species (block, random, etc.). A polymer may have a recognizable repeating structure, such as having a defined backbone, or may have branched and random structure with multiple sets of repeating units or a structure that cannot be easily described due to the randomness. Polymers for use in various embodiments may have undefined molecular size and structure. In instances wherein complete structural elucidation is not possible, polymers may be denoted as having n repeating units, wherein n=1 to infinity. In various embodiments, polymers may also comprise adducts. One such non-limiting example is a grafted polymer formed by derivatization of a parylene polymer with an organosilane.

As used herein, the term "parylene" refers to the broad genus of (poly)-p-xylylene polymers, with the general formula —[$CH_2$—$C_6H_4$—$CH_2$]— representing the unsubstituted polymer referred to as parylene-N. The phenyl ring of the p-xylylene group may be substituted, such as with one chlorine atom (parylene-C), —[$CH_2$—$C_6H_3Cl$—$CH_2$]$_n$—, or two chlorine atoms, (parylene-D), —[$CH_2$—$C_6H_2Cl_2$—$CH_2$]$_n$—. In various embodiments, parylene polymers are grafted with organosilane chains, such as to form parylene polymers having a —$CH_2CH_2CH_2$—$Si(OR^1)_3$ substituent on each one of the p-xylylene repeating groups.

As used herein, the term "alkyl" refers to any linear, branched or cyclic monovalent carbon containing radical, such as, for example, methyl, ethyl, n-propyl, i-propyl, n-butyl, butyl, t-butyl, cyclopropyl, cyclohexyl, and the like. A "substituted alkyl" substituent refers to the above alkyl group that also bears at least one other group including a heteroatom, such as an —OH, —SH, —$OCH_3$ or —$CO_2H$ substituent, or at least one intervening atom positioned in the carbon chain of the alkyl group. Thus, a substituted alkyl group may include such monovalent species as —$CH_2$—O—$CH_3$, and —$CH_2CH_2$—N($CH_3$)—$CH_2CH_3$. Since alkyl groups may be cyclic, "substituted alkyl group" also encompasses all non-aromatic heterocyclic species. A non-limiting example of the latter is a 1-morpholinyl substituent.

When referring to at least two substituents "R" bonded to a common atom, such as $R^9R^{10}R^{11}N$ the option of "cyclic" refers to the situation wherein at least two of the "R" substituents form a ring structure that includes the common atom to which the "R" groups are bonded. Thus, as an example, the genus structure $R^9R^{10}R^{11}$ wherein $R^9$, $R^{10}$, and $R^{11}$ are alkyl, includes N-methylpyrrolidine, amongst many other chemical species.

As used herein, the term "aryl" takes on the ordinary meaning of an aromatic substituent, including phenyl and any heteroaryl, e.g. pyridyl, imidazoyl, and the like. A "substituted aryl" refers to a substituted phenyl group or a substituted heteroaryl moiety, wherein the substitution is in any position around the aromatic ring, and in any combination.

As used herein, the term "nucleophile" takes on the ordinary meaning in organic chemistry, which refers to a substituent capable of donating an electron pair to an electrophilic species to form a chemical bond. Examples of neutral substituents that would be considered nucleophilic substituents attached to a chemical species include, but are not limited to, —OH, —SH, —$NH_2$, —$NHR^8$, and —$NR^9R^{10}$. Thus, a molecular species such as R—OH is considered nucleophilic because it contains the nucleophilic hydroxyl substituent —OH. Anionic substituents are also considered nucleophilic. Examples include, but are not limited to, —$O^-$, —$S^-$, —$CO_2^-$, and the like.

As used herein, the term "leaving group" takes on the ordinary meaning in the field of organic chemistry, which refers to a molecular fragment or substituent that departs from a molecular species with a pair of electrons upon heterolytic bond cleavage. Chemical reactions for use in various embodiments may comprise the reaction between a nucleophile and an electrophilic atom having a leaving group attached thereto, which results in a new bond formed between the nucleophile and the electrophilic atom and the departing of the leaving group (i.e. an $S_N2$-type reaction). As examples for use in various embodiments, an amine (nucleophile) may displace a halogen (leaving group) from a carbon atom resulting in a new C—N bond and the expulsion of the halogen, or a tertiary amine (nucleophile) may displace a halogen (leaving group) from a carbon atom resulting in a new quaternary ammonium compound having C bonded to a positively charged N that has three other appendages (i.e. quaternary). In this case, the halogen is the negatively charged counterion to the quaternary/positively charged N.

As used herein, the term "medical dressing" broadly refers to any and all dry substrates used to cover portions of a patient, including but not limited to, open wounds, treated wounds, suture sites, open surgical sites, scrapes, cuts, scratches, insect bites, acne, breaks, sprains, and joints. The term "dry" indicates that the antimicrobial medical dressings herein are dry to the touch, meaning that although treated to retain antimicrobial activity, the treatment is dried such that the dressing is dry to the touch. The term "dry" is not meant to imply that an antimicrobial coating on a medical dressing is necessary permanent. In other words, it may dissolve out into a wound exudate or other physiological fluid or into surrounding tissue. The medical dressings herein may be hard dressings or soft dressings. In various examples, the medical dressing may be a elastic sleeve such as to support a sprain, or a wrap or undergarment textile for use underneath a hard cast, or a simple adhesive bandage. Some examples include the familiar ACE™ braces, supports, wraps, and sleeves available from 3M®. The medical dressing may be used in and around a medical clinic, an institution of any sort, or at home. The medical dressings may be, for example, the absorbent pads used in surgery and other medical procedures, dry wipers and any other materials to wipe, dab, absorb, clean, scrub, and any gauze material, flexible wrappings or bandages.

As used herein, the term "medical dressing" also includes all medical garments, along with household and institutional dry wipers. One common institutional dry wiper is manufactured and sold by Kimberly-Clark® under the brand name KimWipes®. These wipes are typically cellulosic, and are lint and dust free for critical wiping. Another dry wiper used herein are the WypAll® L40 brand of all purpose wipers from Kimberly-Clark®, comprising a double re-creped cellulose structure. Other familiar dry wipers comprise microfiber substrates, such as for example, Zwipes® microfiber cleaning cloths.

For example, the term "medical dressing" includes, but is not limited to, adhesive bandages, gauze rolls, gauze pads, wraps, sponge material, breathable films, stretch wraps and sleeves, patient gowns, examination gowns, surgical gowns, and dry wiper substrate. Although the medical profession sometimes uses the term "sponge" to refer to a wadded up or folded up multi-ply adsorbent article (such as folded up gauze such as used for dabbing surgical sites), all of these soft flexible substrates are incorporated in the term "medical dressing" herein. More specific examples of medical dressings include, but are not limited to, surgical gauze sponge, cotton rolls, nonwoven sponge, 100% cotton gauze, and adhesive bandages of all shapes and sizes regardless if for professional use or consumer use. As used herein, "substrate" refers to the dry fabric portion of adhesive bandages and such, along with the bulk fabric material (e.g., in rolls) cut up into individual dry wipers. A glimpse of the immense scope of "medical dressings" suitable for use herein is found on the Dynarex® website, www.dynarex.com, in particular, the items found listed under the categories of "patient care", "personal care", "personal protection", and "wound care".

Medical dressings may comprise any type of substrate known in the textile industry, consumer products industry, and the medical profession. Medical dressings may include woven and nonwoven fabrics comprising any combination of natural (e.g., pulp, cotton, etc.), synthetic materials (e.g., polypropylene (PP), polyethylene (PE), etc.), and combinations thereof (e.g., pulp wet laid on a PE webbing).

Medical dressings for use herein may comprise a nonwoven material, such as obtained, for example, by a spunlace, meltblown, wet laid or air laid process using synthetic or natural fibers or filaments, or combinations thereof, wherein the fibers are arranged in parallel or other orientation or disposed randomly. For example, a medical dressing may comprise wet laid, randomized, polyethylene filaments or may comprise woven 100% cotton fibers. Another example of a medical dressing of use herein is a meltblown PP nonwoven wiper available from Kimberly-Clark® under the brand name KIMTECH®. Medical sleeves, such as compression sleeves or an under-the-cast wrap or sleeve may comprise Kevlar® or Spandex®, for example, or any other synthetic or natural material. Medical dressings herein also include cast covers used on the outside of a cast rather than underneath a cast.

In addition to a fabric or fibrous layer, certain medical dressings (most notably bandages) may also include an adhesive polymer, an elastomeric, rubberized, fabric or other flexible backing layer. The medical dressings may also include various coatings such as Teflon® (such as to prevent a dressing from adhering to a wound). Non-limiting examples of medical dressing materials also include cotton, pulp, and synthetics such as polyester, polyethylene, polypropylene and polycarbonate.

Medical dressings such as these and others may be coated as disclosed herein, and the medical dressing thus coated may maintain a residual antimicrobial efficacy on its surfaces throughout any portion of, or all of, the normal use of the dressing before it is disposed of. In various embodiments, coatings on the soft surfaces of a medical dressing remain bonded to the fiber surfaces and retain the residual antimicrobial efficacy in the presence of wound exudate, various external environmental factors (e.g. water), warmth, and perspiration. In other examples, antimicrobial coatings on the soft surfaces of a medical dressing are loosely bonded, if at all, to the fiber surfaces and the antimicrobial coating dissolves over time into the wound exudate. To improve coating attachment and durability, various medical dressings (particularly those comprising polyethylene fibers) may be surface treated (such as by corona treatment) prior to coating with an antimicrobial coating composition. In various embodiments, synthetic fibers (most notably polyethylene) are difficult to wet with aqueous compositions, and thus prior surface treatment of the dressing comprising these fibers helps maximize the coating of individual fibers in a network such as a woven or nonwoven. Medical dressings may also be coated after application to the patient. For example, a wound may be medically triaged and appropriately bandaged, and then an antimicrobial coating composition in accordance to the present disclosure sprayed on top of the bandage and on the skin areas adjacent to the bandaging.

As used herein, the term "antimicrobial" is used generally to indicate at least some degree of microbe kill or mitigation of microbe reproduction by an antimicrobial composition or a residual antimicrobial coating disposed on a soft surface. For example, the term antimicrobial may be used to indicate a bacteriostatic effect, a sanitizing level (3-log, or 99.9%) of reduction in at least one organism, a disinfection level (5-log, or 99.999%) of reduction in at least one organism, or complete sterilization (i.e., no detectable organisms). Microbes, or microorganisms, may include any species of bacteria, virus, mold, yeast, or spore.

The terms "residual antimicrobial," "residual self-sanitizing," and "self-decontaminating surface" are used interchangeably to indicate a soft surface of a medical dressing that maintains antimicrobial efficacy over a certain period of time under certain conditions once the dressing is coated with an antimicrobial coating composition and cured in various manners as disclosed herein. Treated gauze, for example, may maintain residual antimicrobial efficacy indefinitely, or the coating may eventually "wear out" and lose its residual antimicrobial efficacy. In various aspects, a medical dressing may be thrown away before the dressing loses its residual antimicrobial efficacy. For example, an antimicrobial dry wiper may be used just once to absorb a bodily fluid spill, and then immediately disposed of. In that case, the antimicrobial properties of the dry wiper may simply reduce the biohazard level in the trash, although can also reduce the biohazard load in the wiper that could be transferred to the glove of the user. In other example, an antimicrobial bandage retains its antimicrobial efficacy for the day or so, or few days, up to when the bandage is removed from the patient's wound and disposed of.

In various embodiments, a residual antimicrobial coating may be tested at discrete periods of time by inoculating the treated dressing, e.g., gauze, in accordance with American Association of Textile Chemists and Colorists test method "AATCC 100" (entitled "Antibacterial Finishes on Textile Materials: Assessment of") or variations thereof. Other test methods may involve examination of a wound site over time rather than measuring the remaining antimicrobial efficacy of the dressing itself. For example, a wound covered in a residual antimicrobial dressing may be examined microscopically or microbiologically for a reduction in colonization of a particular microorganism. A wound covered during with an antimicrobial bandage or gauze during the healing process may be swabbed for organisms.

As used herein, the term "antimicrobial coating composition" refers to a chemical composition comprising at least one chemical species, which is used to produce a residual antimicrobial coating on a dressing after the composition is applied and then either manually dried, passively allowed to dry, or cured in some manner. However, the term is extended to include a composition that may be applied in a coating sequence (e.g. over or under) or contemporaneously with the application of an antimicrobial coating composition comprising an antimicrobial active, such as to assist in bonding the residual antimicrobial coating to the surface, improve longevity of the overall coating, and/or to provide a catalytic effect or some sort of potentiation or synergy with the residual antimicrobial coating comprising an antimicrobial active. For simplicity, each one of multiple compositions used sequentially or contemporaneously to produce an overall residual antimicrobial coating on a medical dressing is referred to as an "antimicrobial coating composition," regardless if one or more of the compositions used in the coating process has no identifiable antimicrobial active, or where the active agent is uncertain. An antimicrobial coating composition may comprise a neat, 100% active chemical species or may be a solution or suspension of a single chemical species in a solvent. In other aspects, a composition may comprise a complex mixture of chemical substances, some of which may chemically react (hydrolyze, self-condense, etc.) within the composition to produce identifiable or unidentifiable reaction products. For example, a monomeric chemical species in an antimicrobial coating composition may partially or fully polymerize while in solution prior to a coating process using that composition. In various embodiments, chemical constituents within an antimicrobial coating composition may chemically react on the fiber surfaces of the dressing that the composition is applied to, such as while the composition is drying and concentrating on the fibers or while the coating composition is cured by various methods on the fibers. In various examples, the fibers themselves may have certain catalytic effect, such as simple pH effects, which may promote certain chemical reactions and bonding to occur. Antimicrobial coating compositions may further comprise any number and combination of inert excipients, such as for example, solvents, surfactants, emulsifiers, stabilizers, thickeners, free-radical initiators, catalysts, pH adjustors, etc. In various examples, antimicrobial coating compositions disclosed herein include an indicator, such as a dye, that aids in determining coating thickness, uniformity, coverage, durability, presence, and the like. Such an indicator may turn from colorless to colored, or vice versa, when an antimicrobial coating on a medical dressing is no longer present or has become ineffective.

An antimicrobial coating composition herein is usable to form a dry residual antimicrobial coating on the soft surfaces of medical dressings once dried or cured thereon. Such a coating can keep inactivating new microorganisms that come in contact with the dressing. In various embodiments, coating compositions may not become antimicrobial on the dressing until dried or cured thereon, but are nonetheless, still referred to as antimicrobial coating compositions because of their ability to form a residual antimicrobial coating on a dressing. Antimicrobial coating compositions may provide a residual antimicrobial efficacy to medical dressing, meaning that a microorganism later inoculated on, or that otherwise comes in contact with, the coated surface of the dressing may experience cell death, destruction, or inactivation, such as mitigated ability to reproduce to pathogenic levels. The residual antimicrobial effect made possible by the coatings herein is not limited by a particular mechanism of action, and no such theories are proffered. For example, an antimicrobial effect, such as measured by inoculating a coated and dried medical dressing, may be the result of intracellular mutations, inhibition of certain cellular processes, rupture of a cell wall, or a nondescript inactivation of the organism. Other antimicrobial effects may include inhibiting the reproduction of an organism, or inhibiting the organism's ability to accumulate into colonies or other agglomerations.

As used herein, the term "curing" includes all known curing methods in the chemical and engineering arts. These include, but are not limited to, ambient, passive curing, heated manual curing, freeze-drying, radiation curing and chemical curing. For example, an antimicrobial coating composition applied to a medical dressing may be subject to UV, visible light, microwave, ion beam or other incident radiation in order to cure the composition on the fibrous surfaces of the dressing. Drying includes, but is not limited to, heating a coated medical dressing in a convection oven, a vacuum oven, or an autoclave. In other aspects, an antimicrobial coating composition may be applied to a medical dressing and then the dressing dried under ambient conditions. Such ambient or passive drying, drying over a heated roller, or in an oven are all useful methods of curing coatings in a roll coating operation. Roll coating processes find use herein to coat medical dressing substrate in bulk, such as while still in large rolls. Ambient drying conditions may optionally include control of the percent relative humidity (% RH). Curing by any of these methods may be used to drive off volatile components such as solvents including water, and/or initiate and/or catalyze inter- or intra-molecular chemical reactions such as hydrolysis, inter- and intramolecular self-condensation, intermolecular polymerization between different species, or crosslinking of polymer chains, or covalent bonding of chemical entities to the fibers of the dressing. During curing, such as ambient drying, a coating is developed on the medical dressing that is durable to exposure to wound exudate, various environmental factors, warmth and perspiration for a desired period of time, such as the time period the dressing is used prior to disposal. In other examples, curing may comprise simple air drying, and/or coating compositions may be designed such that the antimicrobial coatings on a medical dressing dissolve off into the wound exudate over a period of time.

In various embodiments, antimicrobial coating compositions are applied to medical dressings to produce a residual antimicrobial coating on the dressing. Generally, medical dressings will be fibrous in nature, in that individual fibers within woven or nonwoven networks of fibers are coated with an antimicrobial coating composition. In various embodiments, at least one coating composition is applied to a dressing. The application process may comprise any single application method or a combination of application methods. In various examples, different application methods may be used for each of two or more successive coatings of antimicrobial coating compositions. In various embodiments, at least one coating is applied to a dressing, and in the instances where two or more coatings are applied, the coatings may be chemically the same or different. In various embodiments, any period of time may transpire between separate coatings of a dressing, such as, seconds, minutes, hours, days, or longer.

In various embodiments, any application method used in the textile industry may be used to apply an antimicrobial coating composition to a medical dressing substrate or directly to a finished medical dressing product. Further, antimicrobial coating compositions may be applied to a component of a medical dressing rather than to a finished medical dressing. For example, bulk materials in the form of rolls may be roll coated, and then that coated fabric cut and used to make numerous dressings such as adhesive bandages or rolls of gauze. Coated fabrics may also be used in later lamination processes to produce various medical dressings.

Coating processes can be categorized as including "self-metering systems" that saturate substrates and "pre-metering systems" that allow at least some control over the amount of liquid added to a fabric substrate. In either category, there are various "contact" methods and "non-contact methods," referring to whether a substrate is touched by any equipment during the coating process. Various self-metering coating techniques include, but are not limited to, dipping, soaking, blade coating, and roller coating. Pre-metering techniques include, but are not limited to, gravure roll coating methods, curtain coating and screen roller coating. Depending on the configuration of the rollers, gravure coating may be offset or direct.

Roll coating methods in general have an advantage of being adaptable to roll-to-roll processes, meaning that a roll of fabric substrate is unrolled at the start of the operation, pulled through a coating process and then wound-up at the other end of the operation. Coated rolls may be cured in bulk (e.g. by simply storing rolls of coated fabric under certain conditions), or coated rolls may again be unwound, run through a curing operation and then wound-up at the other end. Coated rolls that are optionally cured may then be shipped to third party manufacturers to complete the production of the medical dressing.

Roll coating methods for use in various embodiments include, but are not limited to, knife coating, direct roll coating, padding, and calendar roll coating. In roll coating in general, a fabric is pulled through a series of rollers that are continually wetted with a composition, or a knife edge pulls a layer of liquid composition over a moving fabric, or a fabric is dipped into a bath of composition and then run between nip rollers. All the methods are designed to apply a desired amount of a composition to a woven or nonwoven fabric. In certain embodiments, the fabric substrate may be completely saturated with an antimicrobial coating composition prior to a curing step.

In various embodiments, a dip coating process is a simple and useful method for coating medical dressings or a fabric starting material for making a medical dressing. Excess liquid composition may be expressed from the material, such as by passing the wetted fabric between nip rollers. Another useful and simple method for coating medical dressings, or the fabric starting material used in making a medical dressing, is to spray one or more antimicrobial coating compositions onto a moving fabric, such as in a roll-to-roll operation. In these embodiments, a spray bar can be positioned perpendicular to the length of the fabric, as wide as the width of the fabric, and over the top of and optionally underneath the fabric in order to spray a prescribed amount of composition onto the moving fabric. The operation may be fine-tuned such that the fabric is coated with a particular weight of composition, such as measured in grams per square meter ($g/m^2$ or "gsm"). When more than one coating composition is to be applied in a roll-to-roll coating operation, two spray bars can be used, one for each composition, positioned at different positions along the moving fabric line. Curing stations can be set up after the first and second coating positions, such as ovens or heated rollers, for example. In this way, a fabric roll can be unrolled, pulled under a first coating bar, pulled through a first curing station, pulled under a second coating bar, pulled through a second curing station, and then wound-up at the end. A roll of fabric treated in this way may comprise, for example, a woven or nonwoven fabric.

In various embodiments, a residual antimicrobial coating on a medical dressing may have unimolecular thickness (i.e., a monolayer), or may be macroscopically thick, such as having microns to millimeters range of thickness. The thickness may be seen on individual fibers within a medical dressing, such as visualized by an increase in the average diameter of the fibers once coated. In various embodiments, a residual antimicrobial coating on fibers or fabrics of a medical dressing is from about 1 nm to about 1 mm in thickness. In other examples, a residual antimicrobial coating is from about 1 nm to about 100 μm in thickness. Coatings may be flexible, durable, and resistant to flaking and chipping. Coatings of unimolecular thickness on fibers are not perceivable to the naked eye, and may be more resistant to flaking and chipping compared to coatings of macroscopic thicknesses, such as when fabric rolls are wound and unwound in roll-to-roll manufacturing processes.

In various embodiments, an antimicrobial coating composition may be packaged for consumer or professional use. For example, an antimicrobial coating composition may be packaged with a propellant in an aerosol package, with the propellant intermixed with the composition or surrounding a bag in a bag-in-can arrangement. Or, an antimicrobial coating composition may be packaged in a non-aerosol pump or trigger sprayer. In this way, the consumer or the practitioner can spray the antimicrobial coating composition directly onto a patient, such as spraying onto a bandage or wrap already in place on the patient, along with the skin areas surrounding the bandage or wrap. Such a spray may be used on the skin, sprayed directly onto a wrap or dressing on either or both sides, or sprayed inside a compression sleeve prior to placement on a patient. In one specific embodiment, a wound is first triaged with sutures and antibiotic and then covered with a dressing. The dressing may or may not comprise an antimicrobial coating. Then, an antimicrobial coating composition packaged in an aerosol or non-aerosol package is sprayed onto the bandage and all around the adjacent areas of the skin. In this way, pathogens are prevented from migrating into the wound site from remote locations on the skin. In other examples, a spray antimicrobial coating composition may be used on a compression sleeve or wrap before a hard cast is applied overtop. Or a spray may be applied to the already hardened cast prior to applying a cast cover. In other aspects, a small spray bottle can be carried by the patient and the patient may apply additional antimicrobial treatment onto the dressing at any time. Any of these procedures, and combinations thereof, may be used to maintain cleanliness of a medical treatment, such as to prevent casts, wraps and sleeves from becoming odorous and unhygienic over time.

Organosilane and Amine Coatings

In various embodiments, an antimicrobial coating composition comprises at least one organosilane of general structure $(R^1O)_3Si—R^2—Z$, or an adduct, hydrolysis product, or polymeric reaction product therefrom, wherein $R^1$ is H, alkyl, substituted alkyl, aryl, or substituted aryl, $R^2$ is a bivalent linker of any molecular chain length and comprises any degree of branching, which may comprise any number of methylene groups $—(CH_2)_n—$, optionally substituted with various substituents such as —OH, —SH, —OCH$_3$, or —CO$_2$H anywhere along the chain, and/or interrupted with intervening heteroatoms and/or degrees of unsaturation, and Z is a nucleophile, a leaving group or a quaternary nitrogen substituent.

An antimicrobial coating composition may further comprise a solvent, such as water and/or an alkanol, and/or any additional excipient such as, but not limited to, a surfactant, a quaternary salt, an inorganic silicate, an inorganic acid, and organic acid, an inorganic base or an organic base. In various examples, an organic base comprises any organic amine, such as diethanolamine or triethanolamine. In other examples, a quaternary salt comprises choline chloride or choline bitartrate.

In certain examples, an antimicrobial coating composition comprises at least one organosilane of general structure $(R^1O)_3Si—R^2—Z$, wherein $R^1$ is H, $CH_3$ or $CH_2CH_3$, $R^2$ is $—CH_2CH_2CH_2—$, and Z is $—NR^{12}R^{13}$, wherein $R^{12}$ and $R^{13}$ are independently H, alkyl, substituted alkyl, aryl, or substituted aryl. In other examples, Z is a halogen. In other more specific examples, $R^2$ is any bivalent linker, and Z is $—NH_2$, $—N(CH_3)_3^+Cl^-$, $—N(CH_3)_2(n-C_{18}H_{37})^+Cl^-$, $—OH$, or $—Cl$. In another specific example, an antimicrobial coating composition comprises at least one organosilane of general structure $(R^1O)_3Si—R^2—Z$, wherein $R^1$ is H, $CH_3$ or $CH_2CH_3$, $R^2$ is $—CH_2CH_2CH_2—$, and Z is $—NH_2$. In yet another specific example, an antimicrobial coating composition comprises at least one organosilane of general structure $(R^1O)_3Si—R^2—Z$, wherein $R^1$ is H, $CH_3$ or $CH_2CH_3$, $R^2$ is $—CH_2CH_2CH_2—$, and Z is $—Cl$.

In various embodiments, an antimicrobial coating composition may comprise at least one of 3-chloropropyltrimethoxysilane, 3-chloropropyltriethoxysilane, 3-chloropropyl silanetriol, 3-aminopropyltrimethoxysilane, 3-aminopropyltriethoxysilane, 3-aminopropylsilanetriol, octadecyldimethyl-(3-trimethoxysilylpropyl) ammonium chloride (CAS No. 27668-52-6), or octadecyldimethyl-(3-trihydroxysilylpropyl) ammonium chloride (CAS No. 199111-50-7). It should be recognized that certain trialkoxysilanes hydrolyze in water at various rates of reaction to the corresponding trihydroxysilane species, which then may go on to self-polymerize into various oligomer distributions.

In various examples, an antimicrobial coating composition further comprises an organic amine. An organic amine for use in various embodiments may be primary, secondary, or tertiary in nature. In general, an organic amine for use in various embodiments may comprise an amine having structure $R^9R^{10}R^{11}N$ wherein $R^9$, $R^{10}$, and $R^{11}$ are independently H, alkyl, substituted alkyl, aryl, substituted aryl or cyclic. The latter option accentuates that an organic amine for use in various embodiments may be cyclic, (i.e. any two of $R^9$, $R^{10}$, and $R^{11}$ may form a ring with the N atom in the ring). Organic amines for use in various embodiments includes ammonia, ($R^9$, $R^{10}$, and $R^{11}$ are each H). In accordance to the general structure provided, an organic amine for use in various embodiments may comprise diethanolamine or triethanolamine, amongst many other species of amines.

In various examples, an antimicrobial coating composition comprises an organosilane of structure $(R^1O)_3Si—R^2—Z$, and at least one organic amine having structure $R^9R^{10}R^{11}N$ wherein $R^1$ is H, alkyl, substituted alkyl, aryl, or substituted aryl, $R^2$ is a bivalent linker Z is a nucleophile, a leaving group, or a quaternary nitrogen substituent, and $R^9$, $R^{10}$, and $R^{11}$ are independently H, alkyl, substituted alkyl, aryl, substituted aryl, or participate in forming a cyclic structure. Depending on the choices for these variables, there may be chemical reactions between the organosilane and the organic amine(s) in solution or on a surface, or no chemical reactions at all.

An antimicrobial coating composition may comprise at least one of 3-chloropropyltrimethoxysilane, 3-chloropropyltriethoxysilane, 3-chloropropyl silanetriol, 3-aminopropyltrimethoxysilane, 3-aminopropyltriethoxysilane, 3-aminopropylsilanetriol, octadecyldimethyl-(3-trimethoxysilylpropyl) ammonium chloride, or octadecyldimethyl-(3-trihydroxysilylpropyl) ammonium chloride, and at least one of diethanolamine or triethanolamine. An antimicrobial coating composition may further comprise any solvent such as water, any alkanol, or any mixture of solvents.

An antimicrobial coating composition may comprise at least one of 3-aminopropyltrimethoxysilane, 3-aminopropyltriethoxysilane, and 3-aminopropylsilanetriol, optionally with a choline salt such as choline chloride or choline bitartrate.

In various examples, an antimicrobial coating composition comprises an organosilane of structure $(R^1O)_3Si—R^2—Z$ that may undergo hydrolysis in aqueous or alkanol solution. For example, an antimicrobial coating composition comprising 3-chloropropyltrimethoxysilane and water may also comprise 3-chloropropylsilanetriol and methanol. In certain embodiments, forming an antimicrobial coating composition comprising 3-chloropropyltrimethoxysilane in water results in an antimicrobial coating composition comprising 3-chloropropylsilanetriol, water, and methanol.

An antimicrobial coating composition comprising an organosilane of structure $(R^1O)_3Si—R^2—Z$ and optionally any other excipient such as an alkanol or amine, may be applied to a medical dressing to form a residual antimicrobial coating on the dressing. Any method of application as disclosed herein, or known in the textile industries, may be used, such as roll-to-roll coating. The treated dressing or fabric starting material for a dressing may then be air dried, heated or exposed to some other radiation to cure the antimicrobial coating composition into a residual antimicrobial coating on the dressing, such as on individual fibers therein. Curing may comprise ambient drying or heated drying such as in a convection oven.

In various embodiments, a residual antimicrobial coating on a medical dressing comprises at least one organosilane of general structure $(R^1O)_3Si—R^2—Z$, or an adduct, hydrolysis product, or polymeric reaction product therefrom, wherein $R^1$ is H, alkyl, substituted alkyl, aryl, or substituted aryl, $R^2$ is a bivalent linker of any molecular chain length, which may comprise any number of methylene groups $—(CH_2)_n—$, optionally substituted with various substituents such as $—OH$, $—SH$, $—OCH_3$, or $—CO_2H$ anywhere along the chain, and/or interrupted with intervening heteroatoms and/or degrees of unsaturation, and Z is a nucleophile, a leaving group or a quaternary nitrogen substituent. In certain examples, a residual antimicrobial coating further comprises an organic amine having structure $R^9R^{10}R^{11}N$ wherein $R^9$, $R^{10}$, and $R^{11}$ are independently H, alkyl, substituted alkyl, aryl or substituted aryl.

A residual antimicrobial coating on a medical dressing comprises a silsesquioxane of structure:

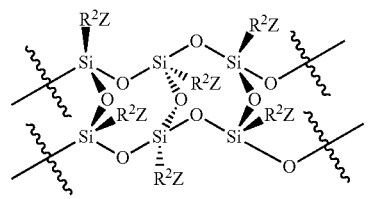

wherein $R^2$ is a bivalent linker of any molecular chain length, which may comprise any number of methylene groups $—(CH_2)_n—$, optionally substituted with various substituents such as $—OH$, $—SH$, $—OCH_3$, or $—CO_2H$ anywhere along the chain, and/or interrupted with intervening heteroatoms and/or degrees of unsaturation, and Z is a nucleophile, a leaving group or a quaternary nitrogen substituent.

A residual antimicrobial coating on a medical dressing comprises an organosilane of structure $(R^1O)_3Si—R^2—Z$, wherein Z is a leaving group. In various examples, Z is —Cl. A residual antimicrobial coating comprises an organosilane of structure $(R^1O)_3Si—R^2—Z$, wherein Z is a halogen X, and a tertiary organic amine $R^9R^{10}R^{11}N$ wherein $R^9$, $R^{10}$, and $R^{11}$ are independently alkyl, substituted alkyl, aryl or substituted aryl.

In various embodiments, a residual antimicrobial coating on a medical dressing comprises $(R^1O)_3Si—R^2—Z$, wherein $R^1$ is H, alkyl, substituted alkyl, aryl, or substituted aryl, $R^2$ is —$CH_2CH_2CH_2$—, and Z is —Cl. In certain examples, the residual antimicrobial coating further comprises an organic amine.

In various embodiments, a residual antimicrobial coating on a medical dressing comprises $(R^1O)_3Si—R^2—Z$, wherein $R^1$ is H or alkyl, $R^2$ is —$CH_2CH_2CH_2$—, and Z is —Cl, and at least one of diethanolamine and triethanolamine.

In various embodiments, a residual antimicrobial coating on a medical dressing comprises the adduct between $(R^1O)_3Si—R^2—Z$, wherein $R^1$ is H, alkyl, substituted alkyl, aryl, or substituted aryl, $R^2$ is a bivalent linker, and Z is a leaving group —X, and an amine of structure $R^9R^{10}R^{11}N$ wherein $R^9$, $R^{10}$, and $R^{11}$ are independently H, alkyl, substituted alkyl, aryl, substituted aryl, or cyclic, having the general structure:

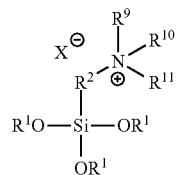

In various embodiments, $R^9$, $R^{10}$ and $R^{11}$ are each —$CH_2CH_2OH$, $R^2$ is any bivalent linker and X=halogen. In other examples, $R^9$ and $R^{10}$ are —$CH_3$, $R^{11}$ is -octadecyl, and X is Cl. In other examples, $R^9$, $R^{10}$ and $R^{11}$ are each —$CH_2CH_2OH$, $R^2$ is —$CH_2CH_2CH_2$—, X=Cl and $R^1$ is H or alkyl. In certain examples, $R^9$, $R^{10}$ and $R^{11}$ are each —$CH_2CH_2OH$, $R^2$ is —$CH_2CH_2CH_2$—, X=Cl, and $R^1$ is —H, —$CH_3$, or —$CH_2CH_3$. In various examples, the above compound is octadecyldimethyl-(3-trimethoxysilylpropyl) ammonium chloride or octadecyldimethyl-(3-trihydroxysilylpropyl) ammonium chloride.

In various embodiments, a residual antimicrobial coating on a medical dressing comprises the adduct between a choline salt and an organosilane $(R^1O)_3Si—R^2—Z$, wherein $R^1$ is H, alkyl, substituted alkyl, aryl, or substituted aryl, $R^2$ is a bivalent linker, and Z is a leaving group. The choline salt may comprise choline chloride, choline bitartrate, or any other choline salt. In specific embodiments, a residual antimicrobial coating comprises the adduct between $(R^1O)_3Si—R^2—Z$ and a choline salt, wherein $R^1$ is H, alkyl, substituted alkyl, aryl, or substituted aryl, $R^2$ is a is —$CH_2CH_2CH_2$—, and Z is a leaving group, with the adduct in the coating having the structure $(R^1O)_3Si—CH_2CH_2CH_2—O—CH_2CH_2—N(CH_3)_3^+X^-$, wherein $R^1$ is H, alkyl, substituted alkyl, aryl, or substituted aryl, and X is Z, the counterion from the starting choline salt, or a mixed salt.

In various embodiments, a residual antimicrobial coating on a medical dressing comprises the adduct:

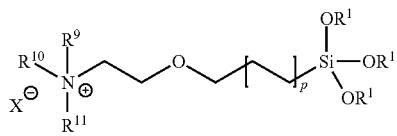

wherein $R^1$ is H, alkyl, substituted alkyl, aryl, or substituted aryl, $R^9$, $R^{10}$ and $R^{11}$ are independently H, alkyl, substituted alkyl, aryl, substituted aryl, or cyclic, X is selected from the group consisting of chlorine, bromine, iodine and bitartrate; and p is from 1 to 5.

In various embodiments, an antimicrobial coating formed from an antimicrobial coating composition comprising an organosilane $(R^1O)_3Si—R^2—Z$ and triethanolamine comprises the polymeric species:

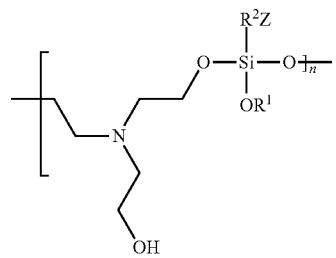

wherein n is from about 1 to about 10.

In various embodiments, an antimicrobial coating formed from an antimicrobial coating composition comprising an organosilane $(R^1O)_3Si—R^2—Z$ and triethanolamine comprises the polymeric species:

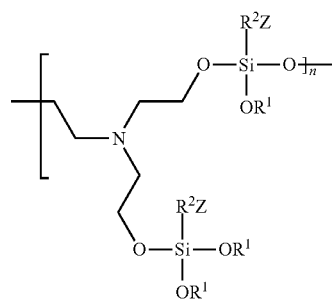

wherein n is from about 1 to about 10.

In various embodiments, an antimicrobial coating formed from an antimicrobial coating composition comprising an organosilane $(R^1O)_3Si—R^2—Z$ and triethanolamine comprises the polymeric species:

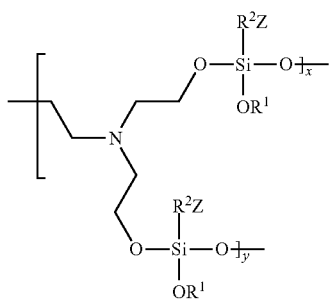

wherein x and y are independently from about 1 to about 10.

In various embodiments, a residual antimicrobial coating formed from an antimicrobial coating composition comprising an organosilane $(R^1O)_3Si-R^2-Z$ and triethanolamine comprises the polymeric species:

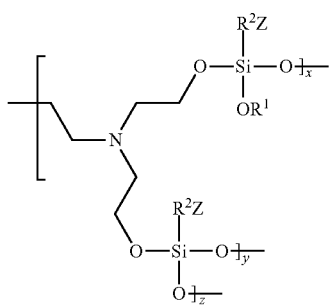

wherein x, y, and z are independently from about 1 to about 10.

In various embodiments, a residual antimicrobial coating composition on a medical dressing comprises an orthosilicate of general structure $(R^1O)_4Si$, wherein $R^1$ is alkyl, substituted alkyl, aryl, or substituted aryl. In various embodiments the antimicrobial coating composition comprises an orthosilicate $(R^1O)_4Si$ and at least one organic amine $R^9R^{10}R^{11}N$, wherein $R^1$ is alkyl, substituted alkyl, aryl, or substituted aryl, and wherein $R^9$, $R^{10}$, and $R^{11}$ are independently H, alkyl, substituted alkyl, aryl, substituted aryl, or cyclic.

In various examples, a residual antimicrobial coating composition on a medical dressing comprises an orthosilicate $(R^1O)_4Si$, and triethanolamine, wherein $R^1$ is alkyl, substituted alkyl, aryl, or substituted aryl. A residual antimicrobial coating formed from this antimicrobial coating composition comprises a crosslinked polymer network with a core structure:

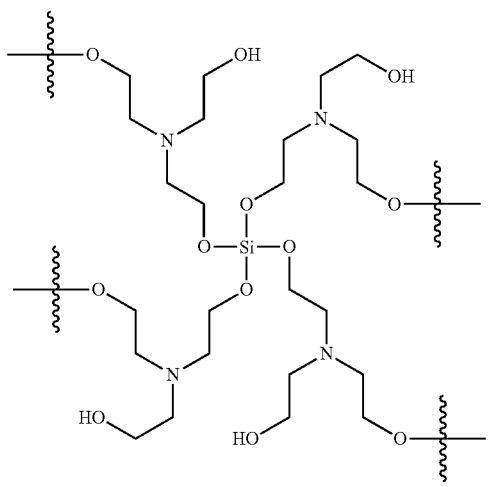 [SMILES: *OCCN(CCO)CCO[Si](OCCN(CCO)CCO*)(OCCN(CCO)CCO*)OCCN(CCO)CCO*]

It is important to note that the polymer formed from an orthosilicate and triethanolamine comprises this structure regardless of the orthosilicate starting material, as noted from the absence of $R^1$ groups in the reaction product. The $R^1O-$ substituents on silicon are exchanged with the hydroxyl substituents of the triethanolamine molecules.

In various examples, an antimicrobial coating composition comprises an orthosilicate $(R^1O)_4Si$, and diethanolamine, wherein $R^1$ is alkyl, substituted alkyl, aryl, or substituted aryl. A residual antimicrobial coating formed from this antimicrobial coating composition comprises a crosslinked polymer network with a core structure:

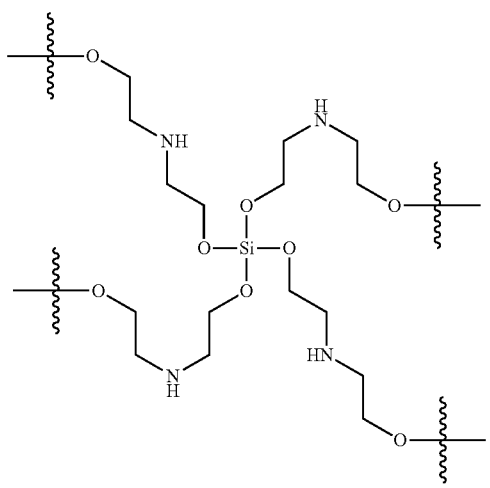 [SMILES: *OCCNCCO[Si](OCCNCCO*)(OCCNCCO*)OCCNCCO*]

The polymer formed from an orthosilicate and diethanolamine has this networked structure regardless of the orthosilicate starting material, as noted from the absence of $R^1$ groups in the reaction product due to the exchange of $R^1O-$ substituents on silicon with the hydroxyl substituents of the diethanolamine molecules.

$TiO_2$, $Ti(OR^3)_4$, and $Ti(OR^3)_4$ Adduct Coatings

In various embodiments, a residual antimicrobial coating is formed on a medical dressing by applying an antimicrobial coating composition comprising at least one Ti(IV) oxide such as $TiO_2$, a $Ti(OR^3)_4$ species, or a dimer, trimer, tetramer or polymer reaction product thereof, or a $Ti(OR^3)_4$ adduct, on the dressing or a fabric starting material to make a dressing, followed by curing including ambient or elevated temperature drying, wherein $R^3$ is alkyl, substituted alkyl, aryl or substituted aryl. As mentioned, formation of a residual antimicrobial coating may comprise this step of applying an antimicrobial coating composition comprising a Ti compound along with the application of at least one additional antimicrobial coating composition to the dressing. The at least one additional antimicrobial coating composition may be applied either before or after the application of the antimicrobial coating composition comprising the Ti compound(s). In examples where more than two coatings are applied to a medical dressing, the other antimicrobial coating compositions and the antimicrobial coating composition comprising the Ti compound(s) may be applied to the medical dressing in any ordered sequence across any timeframe. In various embodiments, the at least one other antimicrobial coating composition comprises an organosilane.

(a) $TiO_2$ Coatings:

In various embodiments, an antimicrobial coating composition comprises $TiO_2$. The $TiO_2$ may be in any physical form, such as for example, anatase. $TiO_2$ for use in various embodiments may comprise rutile, anatase, brookite, hollandite-like, ramsdellite-like, $\alpha$-$PbO_2$— like, baddeleyite-like form, orthorhombic $TiO_2$—OI, cubic, and/or cotunnite-like forms. The most common crystalline forms are anatase, brookite and rutile. Further, an antimicrobial coating composition may comprise a $TiO_2$ sol. Any of these Ti species may be used to form a residual antimicrobial thin film of $TiO_2$ on a medical dressing. To produce such a thin film on a medical dressing, e-beam evaporation, sputtering, chemical vapor deposition, electrostatic spray, or the hydrolytic sol-gel process may be used to form a thin film $TiO_2$ coating from an antimicrobial coating composition.

In certain examples, an antimicrobial coating composition comprises a colloidal suspension of from about 0.5 wt. % to about 50 wt. % $TiO_2$ in water. In other examples, an antimicrobial coating composition comprises an aqueous mixture of Ti—$(O-i-C_3H_7)_4$ usable to create a thin film of $TiO_2$ via the sol-gel process. Such compositions may also comprise an organic solvent, such as an alcohol like n-propanol or n-butanol, a surfactant, or an acid catalyst. In the sol-gel process, $TiO_2$ is prepared by hydrolysis, condensation and polycondensation of a titanium alkoxide, such as Ti—$(O-i-C_3H_7)_4$ or $TiCl_4$. A $TiO_2$ sol-gel composition, when coated onto a medical dressing by spray pyrolysis or other application method, provides a thin film $TiO_2$ coating on the dressing.

In various embodiments, a residual antimicrobial coating comprises $TiO_2$. In other examples, a residual antimicrobial coating comprises $TiO_2$ formed by coating a medical dressing with a colloidal suspension of $TiO_2$ particles. In certain examples, a residual antimicrobial coating comprises $TiO_2$ synthesized by the sol-gel process, as discussed herein above for the titanyl-oxide moieties.

(b) $Ti(OR^3)_4$ Coatings:

In various embodiments, a coating composition comprises $Ti(OR^3)_4$, wherein $R^3$ is alkyl, substituted alkyl, aryl, or substituted aryl, and wherein the four separate $R^3$ groups are identical or different. Examples of $Ti(OR^3)_4$ include, but are not limited to, titanium tetramethoxide, titanium tetraethoxide, titanium methoxide triethoxide, titanium tetra-n-propoxide, titanium tetra-i-propoxide, and titanium tetraphenoxide. Depending on the physical properties of the titanium (IV) species, the compound may be used neat (e.g. Ti—$(O-i-C_3H_7)_4$) as an antimicrobial coating composition or dissolved in an alcohol or other organic solvent(s), such as the corresponding alcohol, where feasible, (methanol, ethanol, i-propanol, etc.). Thus, an antimicrobial coating composition may comprise a solution of Ti—$(O-i-C_3H_7)_4$ in isopropanol or some other alcohol.

In various embodiments, an antimicrobial coating composition comprises $Ti(OR^3)_4$, wherein $R^3$ is alkyl, substituted alkyl, aryl, or substituted aryl. In certain aspects, an antimicrobial coating composition further comprises a solvent selected from the group consisting of water, alkanols, diols, triols, chlorinated organic solvents, ethers, amines, esters, ketones, aldehydes, lactones, phenolics, and mixtures thereof. In certain examples, a solvent is selected from, but not limited to, water, methanol, ethanol, n-propanol, i-propanol, ethylene glycol, 1,2-propanediol, 1,3-propanediol, glycerin, methylene chloride, trichloromethane, carbon tetrachloride, ethylene glycol monoalkyl ether, ethylene glycol dialkylether, propylene glycol monoalkyl ether, propylene glycol dialkyl ether, ethylene glycol monophenyl ether, ethylene glycol diphenyl ether, propylene glycol monophenyl ether, propylene glycol diphenyl ether, diethylether, tetrahydrofuran, pyridine, triethanolamine, diethanolamine, triethylamine, ethylacetate, acetone, furfural, and N-methyl-2-pyrrolidone, and combinations thereof. In various examples, an antimicrobial coating composition consists essentially of Ti—$(O-i-C_3H_7)_4$. Other examples include an antimicrobial coating composition comprising Ti—$(O-i-C_3H_7)_4$ and an alcohol, and a composition comprising Ti—$(O-i-C_3H_7)_4$ and iso-propanol.

In various embodiments, an antimicrobial coating composition comprises $Ti(OR^3)_4$, wherein each $R^3$ is alkyl, substituted alkyl, aryl, or substituted aryl, is applied to at least one surface of a medical dressing in order to provide a residual antimicrobial coating on the dressing. The application method may be a spray method or a dip method of coating. The resulting wetted dressing is then allowed to dry at ambient, or under controlled conditions (e.g. at a particular % RH), or is dried under heated conditions, (e.g. a thermal convection oven) to produce the residual antimicrobial coating on the dressing. The resulting dried coating is substantially free of all solvents. In various examples, an antimicrobial coating composition comprising Ti—$(O-i-C_3H_7)_4$ and an alcohol is applied to a dressing and the alcohol is allowed to evaporate, or alternatively, the dressing is mechanically dried, until the residual antimicrobial coating on the dressing has no more than about 5 wt. % alcohol remaining. In various embodiments, the amount of remaining alcohol after drying is no more than about 1 wt. %. In various embodiments, the amount of remaining alcohol after drying is negligible, (e.g. less than about 0.01 wt. %). In instances wherein the $Ti(OR^3)_4$ species dimerizes, trimerizes, or polymerizes, the resulting moles of alcohol $R^3$—OH is liberated from the fibers of the medical dressing as the coating dries thereon.

In general, the bulkier the $R^3$ groups on $Ti(OR^3)_4$, the more likely the titanium species exists as a monomer, even when dried on a surface. On the other hand, $Ti(OCH_3)_4$, $Ti(OCH_3)(OCH_2CH_3)_3$, and $Ti(OCH_2CH_3)_4$, are known to exist as tetramers in the solid state. Polymerization takes place when titanium alkoxides are hydrolyzed to metal hydroxides or oxides. Thus, for example, the steric size of the $R^3$ groups can be chosen, and the humidity present during drying/curing of a dressing can be controlled, such that monomeric, dimeric, trimeric, tetrameric or polymeric titanium species result on the medical dressing, such as on individual fibers.

In various embodiments, a residual antimicrobial coating on a medical dressing comprises $Ti(OR^3)_4$, wherein each $R^3$ is alkyl, substituted alkyl, aryl, or substituted aryl. In various embodiments, a residual antimicrobial coating on a medical dressing comprises the dimer:

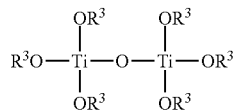

In various embodiments, a residual antimicrobial coating on a dressing comprises the trimer:

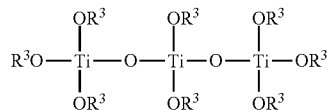

In various embodiments, a residual antimicrobial coating on a dressing comprises the tetramer:

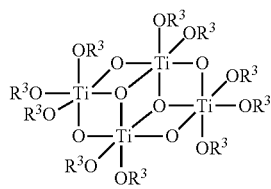

In various embodiments, a residual antimicrobial coating on a medical dressing comprises the linear polymer:

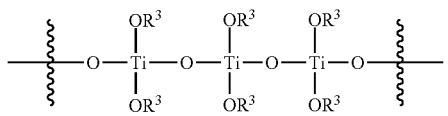

In various embodiments, a residual antimicrobial coating on a medical dressing comprises the crosslinked polymer:

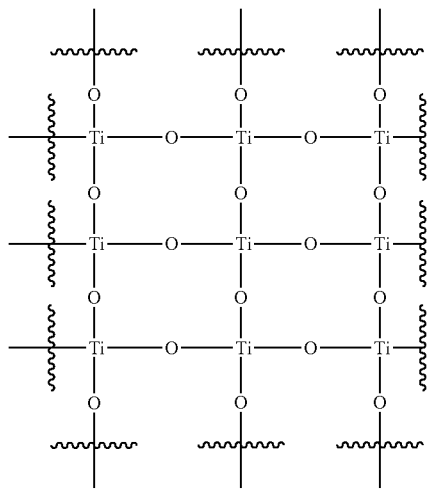

In various embodiments, a residual antimicrobial coating on a medical dressing comprises the polymeric species $Ti_{3(x+1)}O_{4x}(OR^3)_{4(x+3)}$, wherein x=0, 1, 2, . . . , ∞, and wherein $R^3$ is a relatively sterically small substituent, such as methyl, ethyl, n-propyl, and i-propyl, or combinations of these $R^3$ groups.

Other aspects of titanium alkoxide chemistry is disclosed in J. H. Clark, "The Chemistry of Titanium, Zirconium and Hafnium," Pergamon Texts in Inorganic Chemistry, Volume 19, 1973, Pergamon Press, Oxford, England.

(c) $Ti(OR^3)_4$ Adduct Coatings:

In various embodiments, an antimicrobial coating composition for a medical dressing may comprise a titanium (IV) alkoxide and a diol, α-hydroxy acid, or β-hydroxy acid, and optionally any excipient such as solvent, surfactant, acid, or base. These reactants may combine to form various adducts in solution (i.e. within the composition), or may form adducts while curing or once cured onto a medical dressing, such as on the fibers therein. In various examples, an antimicrobial coating composition comprises a titanium (IV) alkoxide, $Ti(OR^3)_4$ wherein each $R^3$ is alkyl, substituted alkyl, aryl, or substituted aryl, and a cis- or trans-1,2-diol, an α-hydroxy acid, or a β-hydroxy acid. When a small molecular weight alcohol is used as a solvent, the $R^3$ groups on the Ti may or may not exchange out with the alcohol. Thus the examples provided below assume there is no alcohol used, or that the alcohol does not exchange out.

A 1,2-diol for use in various embodiments may comprise ethylene glycol, 1,2-propylene glycol, 1,2-dihydroxybutane, and so forth, or any diol of general structure $R^5R^6C(OH)—C(OH)R^7R^8$, wherein $R^5$, $R^6$, $R^7$ and $R^8$ are independently H, alkyl, substituted alkyl, aryl, or substituted aryl. Further, and in accordance to this general structure, a 1,2-diol may comprise a dicarboxylic acid having the general structure:

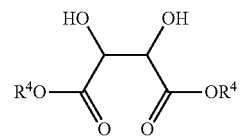

wherein $R^4$=H, alkyl, substituted alkyl, aryl, or substituted aryl. In certain examples, the 1,2-diol comprises tartaric acid or the corresponding mono- or diester.

In other examples, an α-hydroxy acid, such as glycolic acid, lactic acid, citric acid, or mandelic acid, may be used. Further, a β-hydroxy acid, such as salicylic acid, 3-hydroxypropionic acid, or carnitine may be used.

In various examples, an antimicrobial coating composition comprises at least one of $Ti(OR^3)_4$ wherein each $R^3$ is alkyl, substituted alkyl, aryl, or substituted aryl, a cis- or trans-1,2-diol of formula $R^5R^6C(OH)—C(OH)R^7R^8$, and an adduct of general structure:

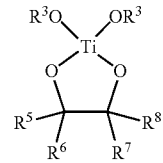

wherein $R^5$, $R^6$, $R^7$ and $R^8$ are independently H, alkyl, substituted alkyl, aryl, or substituted aryl.

In various examples, an antimicrobial coating composition comprises at least one of $Ti(OR^3)_4$ wherein each $R^3$ is alkyl, substituted alkyl, aryl, or substituted aryl, an α-hydroxy acid of formula $R^5R^6C(OH)-CO_2H$, and an adduct of general structure:

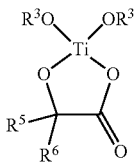

wherein $R^5$, and $R^6$ are independently H, alkyl, substituted alkyl, aryl, or substituted aryl.

In various examples, an antimicrobial coating composition comprises at least one of $Ti(OR^3)_4$ wherein each $R^3$ is alkyl, substituted alkyl, aryl, or substituted aryl, a β-hydroxy acid of formula $R^5R^6C(OH)-C(R^7)(R^8)CO_2H$, and an adduct of general structure:

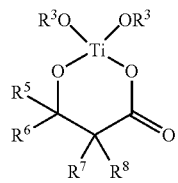

wherein $R^5$, $R^6$, $R^7$ and $R^8$ are independently H, alkyl, substituted alkyl, aryl, or substituted aryl.

In various embodiments, an antimicrobial composition comprising $Ti(OR^3)_4$ wherein each $R^3$ is alkyl, substituted alkyl, aryl, or substituted aryl, and a cis- or trans-1,2-diol, an α-hydroxy acid, or a β-hydroxy acid is applied to a medical dressing to provide a residual antimicrobial coating on the dressing. These compositions may be applied as discussed herein, such as by spray coating or dip coating. The coated dressing may then be cured, such as by ambient drying or oven drying.

In various embodiments, a residual antimicrobial coating comprises a titanium adduct of general structure:

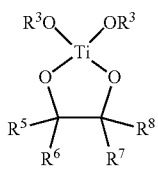

wherein $R^3$ is alkyl, substituted alkyl, aryl, or substituted aryl and $R^5$, $R^6$, $R^7$ and $R^8$ are independently H, alkyl, substituted alkyl, aryl, or substituted aryl.

In various embodiments, a residual antimicrobial coating comprises a titanium adduct of general structure:

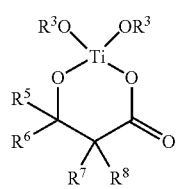

wherein $R^3$ is alkyl, substituted alkyl, aryl, or substituted aryl and $R^5$, $R^6$, $R^7$ and $R^8$ are independently H, alkyl, substituted alkyl, aryl, or substituted aryl.

In various embodiments, a residual antimicrobial coating comprises a titanium adduct of general structure:

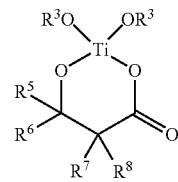

wherein $R^3$ is alkyl, substituted alkyl, aryl, or substituted aryl and $R^5$, $R^6$, $R^7$ and $R^8$ are independently H, alkyl, substituted alkyl, aryl, or substituted aryl.

Coatings Comprising an Organosilane, Amine, and a Titanium Species, or Reaction Products Therefrom, and Organosilane and Amine Coatings in Combination with a Coating Comprising a Titanium Species (a) Antimicrobial Coating Compositions Comprising an Organosilane, an Amine and a Titanium Species:

In various embodiments, an antimicrobial coating composition comprises a mixture of an organosilane structure $(R^1O)_3Si-R^2-Z$, an amine $R^9R^{10}R^{11}N$ and a titanium species $Ti(OR^3)_4$, wherein each $R^1$ is independently H, alkyl, substituted alkyl, aryl, or substituted aryl, $R^2$ is a bivalent linker, each $R^3$ is independently alkyl, substituted alkyl, aryl, or substituted aryl, and $R^9$, $R^{10}$, and $R^{11}$ are independently H, alkyl, substituted alkyl, aryl, substituted aryl, or cyclic. In various examples, a titanium (IV) species comprises the species, $Ti(OR^3)_3O-(CH_2)_q-R^{12}$, wherein $R^{12}$ comprises a chromophore and q is from about 1 to about 10. Chromophore $R^{12}$ may comprise any chromophore that upon exposure to electromagnetic irradiation having a first frequency emits electromagnetic radiation of a second frequency different from the first. In certain embodiments, the first frequency is within the UV spectrum and the second frequency is within the visible spectrum. In certain embodiments, $R^{12}$ comprises a triscyclometalated iridium (III) material that, upon exposure to UV irradiation, emits visible light. A titanium species such as $Ti(OR^3)_4$ or $Ti(OR3)_3O-(CH_2)_q-R^{12}$ may be copolymerized with an organosilane.

When a medical dressing is treated with such a composition and the coating cured thereon, the resulting residual antimicrobial coating formed on the medical dressing may comprise any combination of unreacted organosilane, amine and titanium species along with various hydrolysis products, self-condensation products including homopolymers, intermolecular adducts, and intermolecular polymeric reaction products of various linear, branched and dendritic structure.

In various embodiments, a residual antimicrobial coating comprises a polymer having the structure:

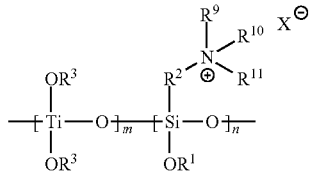

wherein m and n are independently from 1 to about 500.

In various embodiments, an antimicrobial coating composition comprises an organosilane $(R^1O)_3Si—R^2—Z$, an amine $R^9R^{10}R^{11}N$ and a titanium species $Ti(OR^3)_3O—(CH_2)_q—R^{12}$, wherein each $R^1$ is independently H, alkyl, substituted alkyl, aryl, or substituted aryl, $R^2$ is a bivalent linker, each $R^3$ is independently alkyl, substituted alkyl, aryl, or substituted aryl, $R^9$, $R^{10}$ and $R^{11}$ are independently H, alkyl, substituted alkyl, aryl, substituted aryl, or cyclic, $R^{12}$ is a chromophore, and q is from about 1 to about 10.

When this antimicrobial coating composition is coated on a medical dressing and cured thereon, the resulting residual antimicrobial coating comprises a polymer having structure:

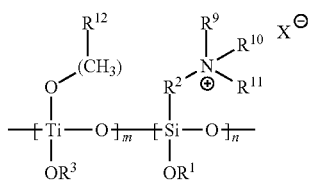

wherein m and n are independently from 1 to about 500. These polymers may comprise linear or crosslinked structures. In more specific examples, $R^2$ is $—CH_2—$, $—CH_2CH_2—$, $—CH_2CH_2CH_2—$, or $—CH_2CH_2—O—CH_2(CH_2CH_2)p-$, wherein p is from 0 to about 5.

(b) Residual Antimicrobial Coatings Comprising an Organosilane and Amine Coating in Combination with a Coating Comprising a Titanium Species:

In certain aspects, a residual antimicrobial coating formed from an antimicrobial coating composition comprising an organosilane $(R^1O)_3Si—R^2—Z$ and an amine $R^9R^{10}R^{11}N$, may further comprise a coating obtained by using an antimicrobial coating composition comprising any titanium species including any form of $TiO_2$, any Ti (IV) oxide, titanyl-oxide moieties, $Ti(OR^3)_4$ or compounds such as $Ti(OR^3)_3O—(CH_2)_q—R^{12}$. The coating comprising the at least one titanium species may be disposed underneath or overtop of an organosilane/amine coating. For example, an organosilane/amine layer may be disposed between the fiber surfaces of the medical dressing and the Ti species layer. There may be any number of organosilane/amine coatings and titanium species coatings, disposed in any order of the layers. Further, any degree of curing may be used for any of the coatings, and each of the coatings may be spaced apart by any time period, such as seconds, minutes, hours, days, months, etc. As mentioned, multiple coating and curing operations are especially amenable to roll-to-roll coating operations as in the textile industry.

As discussed, when various antimicrobial coating compositions dry and/or are cured by other methods on a medical dressing, reactions may take place between the organosilane and the amine, between the amine and the titanium species, between the organosilane and the titanium species, or between all three. In various embodiments, the nature of the fibers in a medical dressing may take part in catalyzing certain reactions.

Organosilane Coating, Overcoated or Undercoated with a Titanium Species

In certain aspects, a residual antimicrobial coating formed from an antimicrobial coating composition comprising an organosilane $(R^1O)_3Si—R^2—Z$ may further comprise a coating obtained by casting an antimicrobial coating composition comprising any titanium species including any form of $TiO_2$, any Ti (IV) oxide, titanyl-oxide moieties, $Ti(OR^3)_4$ or compounds such as $Ti(OR^3)_3O—(CH_2)_q—R^{12}$. The coating comprising the at least one titanium species may be disposed underneath or overtop of an organosilane coating. There may be any number of organosilane coatings and titanium species coatings, disposed in any order of the layers. Further, any degree of curing may be used for any of the coatings, and each of the coatings may be spaced apart by any time period, such as seconds, minutes, hours, days, months, etc. As mentioned, multiple coating and curing operations are especially amenable to roll-to-roll coating operations as in the textile industry.

As discussed, when various antimicrobial coating compositions dry and/or are cured by other methods on a dressing, reactions may take place between the organosilane and the titanium species, and any one of these reactions may be assisted by the nature of the fibers in the dressing.

Grafted Parylene Polymer Coatings
Palladium Catalyzed Amination of Parylene C:

In various embodiments, an antimicrobial coating composition comprises the reaction product between parylene C and at least one organosilane $(R^1O)_3Si—R^2—Z$, wherein each $R^1$ is independently H, alkyl, substituted alkyl, aryl, or substituted aryl, $R^2$ is a bivalent linker and Z is $—NH_2$. The grafted polymer may be produced by the Buchwald-Hartwig cross-coupling reaction, whereby the organosilane $(R^1O)_3Si—R^2—Z$ is reacted with parylene C in the presence of a palladium catalyst such as $PdCl_2$ (dppf). The polymer thus obtained comprises the structure:

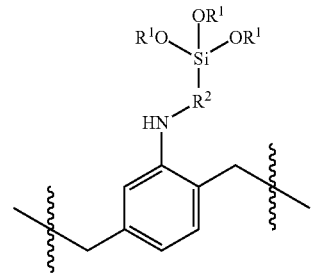

An antimicrobial coating composition comprising this polymer may be applied to a medical dressing using any of the methods described herein.

In various embodiments of the present invention, a coating composition comprises a polymer:

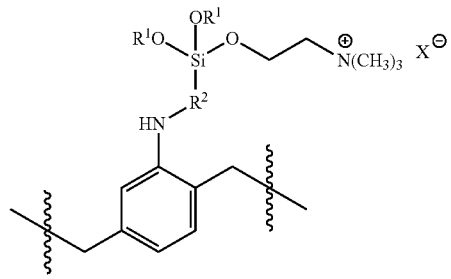

wherein $R^1$ is independently H, alkyl, substituted alkyl, aryl, or substituted aryl, $R^2$ is a bivalent linker, and X is chloride or bitartrate. This parylene polymer may be produced by reacting the grafted polymer with a choline salt such as choline chloride or choline bartartrate. An antimicrobial coating composition comprising this polymer may be applied to a medical dressing by any of the methods described herein.

Other grafted parylene polymers:

Other grafted polymers based on the parylene structure may be envisioned, and may use parylene C, parylene D or any other parylene as the starting material and an organosilane of general structure $(R^1O)_3Si$—$R^2$—$Z$, wherein each $R^1$ is independently H, alkyl, substituted alkyl, aryl, or substituted aryl, $R^2$ is a bivalent linker and Z is a nucleophile or leaving group.

EXAMPLES

Formulations

In the examples, three separate coating compositions were prepared and given internal designations 2030-1, 2030-2 and 2015, as follows:

Formulation designated 2030-1 was prepared by combining 5% v/v of 3-aminopropyltriethoxysilane (herein "APTES"), and 5% v/v triethanolamine (herein "TEA"), remainder water.

Formulation designated 2030-2 was prepared by combining 10% v/v APTES and 0.28% v/v TEA, remainder water.

Formulation designated 2015 was prepared by combining 0.75 wt. % octadecyldimethyl-(3-trimethoxysilylpropyl) ammonium chloride (herein "DMOD"), 0.12 wt. % 3-chloropropyltrimethoxysilane (herein "CPTMS"), and 0.045 wt. % TEA, remainder water.

Substrates

In the Examples, the three following substrates were used:

Dynarex® 3252 nonwoven sponge, 4-ply, polyester blend, available from The Dynarex Corporation, Orangeburg, N.Y. This material is described as being made of parallel laid, cross laid, or randomly laid webs bonded with application of adhesive or thermoplastic fibers under application of heat and pressure. The product is further described as a "polyester blend." This type of nonwoven sponge is used for wound dressing, prepping, scrubbing, and general purpose cleansing.

Caring® PRM21448 woven gauze sponge, 8-ply, 100% cotton, available from Medline Industries, Inc.

WypAll® wiper L40, single-ply, cellulose with a double re-creped structure for added absorbency, available from Kimberly-Clark®.

In certain instances, these substrates were folded to double the ply thickness and/or cut to a specific size for testing, as indicated.

General Procedures

These laboratory methods are designed to mimic industrial processes whereby rolls of substrate may be dipped through a trough of coating formulation or sprayed with a coating formulation as material is passed underneath and/or above a spray bar. Further, the spray method below is designed to mimic the product described above for spraying onto a bandage, wrap, sleeve or other medical dressing when already on the patient.

(1) Dip Coating Procedure:

One piece of the test substrate with size/ply indicated was placed in a sterile petri dish. The designated formulation was pipetted on the test substrate to saturate the material. The amounts for saturation are indicated in the examples (e.g., 3.2 to 5 mL). The saturated test samples were then left in the petri dishes for 1-day to dry prior to any antimicrobial testing.

(2) Spray Coating Procedure:

One piece of the test substrate with size/ply indicated was placed in a sterile petri dish. The designated formulation was sprayed onto both the front and the back of the test substrate with the number of spray pumps indicated in the examples. A regular non-aerosol pump sprayer was used (e.g., 6-8 pump sprays). The saturated test samples were then left in the petri dishes for 1-day to dry prior to any antimicrobial testing.

Sanitizer Test—Version 1

1. A frozen aliquot of S. epidermidis ATCC 12228 was thawed, a loop was streaked on a TSA plate, and incubated for 48 hours at 37° C.

2. One colony from the plate was inoculated in 20 ml of tryptic soy broth (TSB), and incubated for 24 hours at 37° C.

3. The culture was diluted 1:1000 in tryptic soy broth (TSB) to give an inoculum of $1 \times 10^6$ CFU/ml.

4. Swatches were stacked into sterile 180 ml glass jars with screw tops.

5. One set of uncoated control swatches for each material type and contact time was inoculated with 1 ml of prepared bacterial inoculum. The inoculum was deposited onto the swatches in a drop-wise fashion until the full 1 ml was deposited.

6. Time zero (0 h) control swatches were immediately neutralized with 100 ml of sterile letheen broth. The screw tops were tightened, and the jars were shaken vigorously by hand for 1 min. Serial dilutions in PBS buffer were pour-plated at $10^{-2}$ to $10^{-3}$ with cooling TSA.

7. Test swatches were inoculated with the same method as the control swatches. After all swatches were inoculated, the jars were placed into the incubator at 37° C. until the contact time of 1, 4, and 24 h.

8. At completion of contact times, the swatches were neutralized as above. Uncoated control swatches were pour plated at $10^{-2}$ to $10^{-3}$, and coated swatches were pour plated at $10^0$ to $10^{-2}$.

9. The plates were inverted and incubated at 37° C. for 48 h, and then scored by directly counting the colonies.

10. $\text{Log}_{10}$ and percent reductions were calculated relative to the timed controls.

Sanitizer Test—Version 2

The test method used was a modified version of AATCC 100 ("Antibacterial Finishes on Textile Materials: Assessment of"). The test organisms were E. coli 25922 and S. aureus 6538. In accordance to AATCC 100, a 1 mL aliquot of inoculum is added to the test swatch such that the fabric absorbs the inoculum without free liquid present.

Neutralization Validation

1. Uncoated and coated swatches of each test material in jars were neutralized with 100 ml of letheen broth, shaken for 1 min, and allowed to sit undisturbed for 5 min.

2. A dilution of the inoculum (about 1000 CFU/ml) was made and 1 ml added to the jars. After addition of inoculum, jars were left to sit undisturbed for 10 min.

3. From each control and test jar, 0.1 ml or 1 ml was pour plated with TSA. All plates were incubated at 37° C. for 48 h.

4. Control and test plates were scored by directly counting the colonies. For neutralization to be valid, test plates had to contain a 70% or greater colony count when compared to the control plates.

Example 1

Nonwoven Sponge/2030-1

As a test substrate, a 2"×2" (4 sq. in.) sample of Dynarex® 3252 nonwoven 4-ply sponge was used. 5 mL of the 2030-1 formulation was used to saturate each nonwoven test substrate swatch. The test substrates were deemed to be thoroughly dry prior to antimicrobial testing.

The Sanitization Test—Version 2 was used (a modified version of AATCC 100 ("Antibacterial Finishes on Textile Materials: Assessment of"). The test organisms were *E. coli* 25922 and *S. aureus* 6538.

TABLES 1-5 set forth the results from inoculating the dry test substrates with *E. coli.* 25922, (resident times=0, 1 hr., 4 hr., 8 hr., and 24 hr., respectively). TABLES 6-10 set forth the results from inoculating the dry test substrates with *S. aureus* 6538, (resident times=0, 1 hr., 4 hr., 8 hr., and 24 hr., respectively).

In the "Sample" column of each table, "CTRL" refers to a control sample of Dynarex 3252 nonwoven not previously treated with the 2030-1 organosilane/amine antimicrobial coating composition, whereas "TEST" indicates a sample of Dynarex 3252 nonwoven treated with the 2030-1 formulation as described. "R1" and "R2" designate the replicate test numbers, (and should in no way be confused with substituents of the chemical structures herein). In all cases, two replicate tests (designated R1 and R2) were conducted on each of the CTRL and TEST nonwoven samples. Further, "N/A" refers to "not applicable," and "N.D." refers to not determined (e.g., if the test carrier enumerations were greater than the "time zero" or "timed control" enumerations, then the reductions were not calculated).

TABLE 1

Time-Kill Study-*E. coli* 25922-Time Zero data

| Sample | Bacterial Counts (CFU/Carrier) | Mean Count (CFU/Carrier) | $Log_{10}$ Reduction | Percent Reduction |
|---|---|---|---|---|
| CTRL-R1 | 3.90E+06 | 3.97E+06 | N/A | |
| CTRL R2 | 4.05E+06 | | | |
| TEST R1 | 2.75E+06 | 3.23E+06 | N/A | |
| TEST R2 | 3.80E+06 | | | |

TABLE 2

Time-Kill Study-*E. coli* 25922-Time = 1 hr. contact time

| Sample | Bacterial Counts (CFU/Carrier) | Mean Count (CFU/Carrier) | $Log_{10}$ Reduction Relative to Time Zero | Percent Reduction Relative to Time Zero | $Log_{10}$ Reduction Relative to Timed Control | Percent Reduction Relative to Timed Control |
|---|---|---|---|---|---|---|
| CTRL-R1 | 2.07E+07 | 2.07E+07 | N.D. | N.D. | N/A | N/A |
| CTRL R2 | 2.08E+07 | | | | | |
| TEST R1 | 6.55E+05 | 5.92E+05 | 0.83 | 85% | 1.54 | 97% |
| TEST R2 | 5.35E+05 | | | | | |

TABLE 3

Time-Kill Study-*E. coli* 25922-Time = 4 hr. contact time

| Sample | Bacterial Counts (CFU/Carrier) | Mean Count (CFU/Carrier) | $Log_{10}$ Reduction Relative to Time Zero | Percent Reduction Relative to Time Zero | $Log_{10}$ Reduction Relative to Timed Control | Percent Reduction Relative to Timed Control |
|---|---|---|---|---|---|---|
| CTRL-R1 | 4.05E+06 | 4.05E+06 | N.D. | N.D. | N/A | N/A |
| CTRL R2 | 4.05E+06 | | | | | |
| TEST R1 | 4.35E+04 | 5.71E+04 | 1.84 | 98.6% | 1.85 | 98.6% |
| TEST R2 | 7.50E+04 | | | | | |

TABLE 4

Time-Kill Study-*E. coli* 25922-Time = 8 hr. contact time

| Sample | Bacterial Counts (CFU/Carrier) | Mean Count (CFU/Carrier) | $Log_{10}$ Reduction Relative to Time Zero | Percent Reduction Relative to Time Zero | $Log_{10}$ Reduction Relative to Timed Control | Percent Reduction Relative to Timed Control |
|---|---|---|---|---|---|---|
| CTRL-R1 | 3.75E+07 | 3.92E+07 | N.D. | N.D. | N/A | N/A |
| CTRL R2 | 4.10E+07 | | | | | |
| TEST R1 | ≤5.00E+01 | ≤5.00E+01 | >4.90 | >99.9987% | >4.90 | >99.9987% |
| TEST R2 | ≤5.00E+01 | | | | | |

TABLE 5

Time-Kill Study-*E. coli* 25922-Time = 24 hr. contact time

| Sample | Bacterial Counts (CFU/Carrier) | Mean Count (CFU/Carrier) | $Log_{10}$ Reduction Relative to Time Zero | Percent Reduction Relative to Time Zero | $Log_{10}$ Reduction Relative to Timed Control | Percent Reduction Relative to Timed Control |
|---|---|---|---|---|---|---|
| CTRL-R1 | 7.86E+07 | 8.32E+07 | N.D. | N.D. | N/A | N/A |
| CTRL R2 | 8.80E+07 | | | | | |
| TEST R1 | ≤5.00E+01 | ≤5.00E+01 | >4.90 | >99.9987% | >6.22 | >99.99994% |
| TEST R2 | ≤5.00E+01 | | | | | |

TABLE 6

Time-Kill Study-*S. aureus* 6538-Time Zero data

| Sample | Bacterial Counts (CFU/Carrier) | Mean Count (CFU/Carrier) | $Log_{10}$ Reduction | Percent Reduction |
|---|---|---|---|---|
| CTRL-R1 | 3.00E+06 | 3.02E+06 | N/A | |
| CTRL R2 | 3.05E+06 | | | |
| TEST R1 | 2.45E+05 | 2.21E+05 | N/A | |
| TEST R2 | 2.00E+05 | | | |

TABLE 7

Time-Kill Study-*S. aureus* 6538-Time = 1 hr. contact time

| Sample | Bacterial Counts (CFU/Carrier) | Mean Count (CFU/Carrier) | $Log_{10}$ Reduction Relative to Time Zero | Percent Reduction Relative to Time Zero | $Log_{10}$ Reduction Relative to Timed Control | Percent Reduction Relative to Timed Control |
|---|---|---|---|---|---|---|
| CTRL-R1 | 9.15E+06 | 1.03E+07 | N.D. | N.D. | N/A | N/A |
| CTRL R2 | 1.16E+07 | | | | | |
| TEST R1 | 1.95E+05 | 1.56E+05 | N.D. | N.D. | 1.82 | 98% |
| TEST R2 | 1.25E+05 | | | | | |

TABLE 8

Time-Kill Study-*S. aureus* 6538-Time = 4 hr. contact time

| Sample | Bacterial Counts (CFU/Carrier) | Mean Count (CFU/Carrier) | $Log_{10}$ Reduction Relative to Time Zero | Percent Reduction Relative to Time Zero | $Log_{10}$ Reduction Relative to Timed Control | Percent Reduction Relative to Timed Control |
|---|---|---|---|---|---|---|
| CTRL-R1 | 4.20E+06 | 3.81E+06 | N.D. | N.D. | N/A | N/A |
| CTRL R2 | 3.45E+06 | | | | | |
| TEST R1 | 1.56E+05 | 1.51E+05 | 1.30 | 95% | 1.40 | 96% |
| TEST R2 | 1.47E+05 | | | | | |

TABLE 9

Time-Kill Study-*S. aureus* 6538-Time = 8 hr. contact time

| Sample | Bacterial Counts (CFU/Carrier) | Mean Count (CFU/Carrier) | $Log_{10}$ Reduction Relative to Time Zero | Percent Reduction Relative to Time Zero | $Log_{10}$ Reduction Relative to Timed Control | Percent Reduction Relative to Timed Control |
|---|---|---|---|---|---|---|
| CTRL-R1 | 7.35E+06 | 7.20E+06 | N.D. | N.D. | N/A | N/A |
| CTRL R2 | 7.05E+06 | | | | | |
| TEST R1 | 2.55E+04 | 2.57E+04 | 2.07 | 99.1% | 2.45 | 99.6% |
| TEST R2 | 2.60E+04 | | | | | |

TABLE 10

Time-Kill Study-*S. aureus* 6538-Time = 24 hr. contact time

| Sample | Bacterial Counts (CFU/Carrier) | Mean Count (CFU/Carrier) | Log$_{10}$ Reduction Relative to Time Zero | Percent Reduction Relative to Time Zero | Log$_{10}$ Reduction Relative to Timed Control | Percent Reduction Relative to Timed Control |
|---|---|---|---|---|---|---|
| CTRL-R1 | 1.16E+08 | 1.12E+08 | N.D. | N.D. | N/A | N/A |
| CTRL R2 | 1.07E+08 | | | | | |
| TEST R1 | 5.00E+01 | 8.66E+01 | 4.54 | 99.997% | 6.11 | 99.99992% |
| TEST R2 | 1.50E+02 | | | | | |

The results indicated extended residual antimicrobial efficacy on the Dynarex® 3252 nonwoven sponge material when treated with the 2030-1 formulation. This is a remarkable and unexpected outcome for this type of medical dressing, in that the bonding between an organosilane such as $(R^1O)_3Si$—$R^2$—$NH_2$ (i.e., APTES in this case) and polyester, or bonding between a hypothetical adduct formed from APTES and TEA, having a structure $(R^1O)_3Si$—$R^2$—$NR^9R^{10}R^{11+}X^-$, and polyester, would not be expected to be strong in the absence of free and reactive —OH groups on the substrate fabric, which is the case for polyester. These results demonstrate that nonwoven gauze (polyester) treated with a solution of 3-aminopropyltrimethoxysilane and triethanolamine will find use as an antimicrobial wound dressing capable of mitigating the colonization of both *E. coli* and *Staph.* organisms potentially present on or in the wound situs.

Example 2

Nonwoven Sponge/2030-2

Example 1 was modified in that the formulation used to treat the Dynarex® 3252 nonwoven was the 2030-2 formulation instead of the 2030-1 formulation, (thus a different ratio of APTES and TEA in the formulation versus what was used in Example 1). Also, the 4-ply Dynarex® 3252 nonwoven product was folded such that each test swatch was 2"×2" (4 sq. in.) 8-ply. For the dip procedure, 4.5 mL of the 2030-2 formulation was used to saturate each Dynarex® 3252 nonwoven test substrate swatch. In the spray procedure, 6 pump sprays of the 2030-2 formulation were applied to each test substrate. The test substrates were deemed to be thoroughly dry prior to antimicrobial testing.

Further for this Example 2, Sanitization Test—Version 1 was used as described above, with *S. epidermidis* 12228 as the test organism. TABLE 11 sets forth the results from inoculating the dry test substrates with *S. epidermidis* 12228, (resident times=0, 1 hr., 4 hr., and 24 hr., respectively). Log and percent reduction were compared to time control group (uncoated test substrate swatches). Two replicates (N=2) swatches were used for both the uncoated and coated groups. The detection limit was 1 bacterium in 100 mL neutralizer broth=100 CFU/carrier.

TABLE 11

Time-Kill Study-*S. epidermidis* 12228-Time = 0, 1, 4, 24 hr. contact time

| Sample | Application Method | Contact Time (hr) | Mean Count (CFU/Carrier) | Log$_{10}$ Reduction | Percent Reduction |
|---|---|---|---|---|---|
| Uncoated | N/A | 0 | 1.39E+06 | N/A | |
| Dynarex ® 3252 | | 1 | 1.14E+06 | N/A | |
| nonwoven | | 4 | 2.06E+06 | N/A | |
| | | 24 | 5.00E+06 | N/A | |

TABLE 11-continued

Time-Kill Study-*S. epidermidis* 12228-Time = 0, 1, 4, 24 hr. contact time

| Sample | Application Method | Contact Time (hr) | Mean Count (CFU/Carrier) | $Log_{10}$ Reduction | Percent Reduction |
|---|---|---|---|---|---|
| 2030-2 coated Dynarex ® 3252 nonwoven | Dip | 1 | 3.61E+02 | 3.50 | 99.97% |
| | | 4 | 2.55E+02 | 3.91 | 99.988% |
| | | 24 | 1.00E+02 | 4.70 | 99.998% |
| | Spray | 1 | 3.54E+03 | 2.51 | 99.69% |
| | | 4 | 1.00E+02 | 4.31 | 99.995% |
| | | 24 | 1.00E+02 | 4.70 | 99.998% |

The results in TABLE 11 indicate potent residual antimicrobial efficacy on the Dynarex® 3252 nonwoven substrate when treated with the 2030-2 formulation. These results demonstrate that polyester nonwoven gauze treated with a solution of 3-aminopropyltrimethoxysilane and triethanolamine will find use as an antimicrobial wound dressing capable of mitigating the colonization of *Staph.* organisms potentially present on or in the wound situs.

Example 3

Nonwoven Sponge/2015

Example 1 was modified in that the formulation used to treat the Dynarex® 3252 nonwoven was the 2015 formulation, i.e., a mixture of octadecyldimethyl-(3-trimethoxysilylpropyl) ammonium chloride, 0.12 wt. % 3-chloropropyltrimethoxysilane, and 0.045 wt. % TEA. Also, the 4-ply Dynarex® 3252 nonwoven product was folded such that each test swatch was 2"×2" (4 sq. in.) 8-ply. For the dip procedure, 4.5 mL of the 2015 formulation was used to saturate each Dynarex® 3252 nonwoven test substrate swatch. In the spray procedure, 6 pump sprays of the 2015 formulation were applied to each test substrate. The test substrates were deemed to be thoroughly dry prior to antimicrobial testing.

For this example, Sanitization Test—Version 1 was used as described above, with *S. epidermidis* 12228 as the test organism. TABLE 12 sets forth the results from inoculating the dry test substrates with *S. epidermidis* 12228, (resident times=0, 1 hr., 4 hr., and 24 hr., respectively). Log and percent reduction were compared to time control group (uncoated test substrate swatches). Two replicates (N=2) swatches were used for both the uncoated and coated groups. The detection limit was 1 bacterium in 100 mL neutralizer broth=100 CFU/carrier.

TABLE 12

Time-Kill Study-*S. epidermidis* 12228-Time = 0, 1, 4, 24 hr. contact time

| Sample | Application Method | Contact Time (hr) | Mean Count (CFU/Carrier) | $Log_{10}$ Reduction | Percent Reduction |
|---|---|---|---|---|---|
| Uncoated Dynarex ® 3252 nonwoven | N/A | 0 | 1.39E+06 | N/A | |
| | | 1 | 1.14E+06 | N/A | |
| | | 4 | 2.06E+06 | N/A | |
| | | 24 | 5.00E+06 | N/A | |
| 2015 coated Dynarex ® 3252 nonwoven | Dip | 1 | 1.22E+02 | 3.97 | 99.99% |
| | | 4 | 1.00E+02 | 4.31 | 99.995% |
| | | 24 | 1.00E+02 | 4.70 | 99.998% |
| | Spray | 1 | 4.05E+03 | 2.45 | 99.65% |
| | | 4 | 1.32E+03 | 3.19 | 99.94% |
| | | 24 | 5.48E+02 | 3.96 | 99.99% |

The results in TABLE 12 indicate an unexpected level of residual antimicrobial efficacy on the Dynarex® 3252 nonwoven substrate when treated with the 2015 formulation. This result is unexpected in that octadecyldimethyl-(3-trimethoxysilylpropyl) ammonium chloride alone is not known as capable of providing 3-4 log kill as a residual sanitizer. Although not wishing to be bound by any theories, it is at least possible that the presence of the additional CPTMS, and/or the triethanolamine, augments the residual efficacy of the octadecyldimethyl-(3-trimethoxysilylpropyl) ammonium chloride.

These results demonstrate that nonwoven gauze (polyester) treated with a solution of octadecyldimethyl-(3-trimethoxysilylpropyl) ammonium chloride, 3-chloropropyltrimethoxysilane and triethanolamine will find use as an antimicrobial wound dressing capable of mitigating the colonization of *Staph.* organisms potentially present on or in the wound situs.

Example 4

Woven Sponge/2030-2

As a test substrate, a 2"×2" (4 sq. in.) sample of Caring® PRM21448 8-ply woven (100% cotton) sponge, folded to total 16-ply was used. For the dip procedure, 3.2 mL of the 2030-2 formulation was used to saturate each woven cotton test substrate swatch. In the spray procedure, 6 pump sprays of the 2030-2 formulation were applied to each test substrate. The test substrates were deemed to be thoroughly dry prior to antimicrobial testing.

For this example, the Sanitization Test—Version 1 was used as described above, with *S. epidermidis* 12228 as the test organism. TABLE 13 sets forth the results from inoculating the dry test substrates with *S. epidermidis* 12228, (resident times=0, 1 hr., 4 hr., and 24 hr., respectively). Log and percent reduction were compared to time control group (uncoated test substrate swatches). Two replicates (N=2) swatches were used for both the uncoated and coated groups. The detection limit was 1 bacterium in 100 mL neutralizer broth=100 CFU/carrier.

TABLE 13

| Time-Kill Study-*S. epidermidis* 12228-Time = 0, 1, 4, 24 hr. contact time | | | | | |
| --- | --- | --- | --- | --- | --- |
| Sample | Application Method | Contact Time (hr) | Mean Count (CFU/Carrier) | $Log_{10}$ Reduction | Percent Reduction |
| Uncoated Caring ® PRM21448 100% cotton | N/A | 0 | 1.34E+06 | N/A | |
| | | 1 | 1.00E+06 | N/A | |
| | | 4 | 1.85E+06 | N/A | |
| | | 24 | 5.00E+06 | N/A | |
| 2030-2 coated Caring ® PRM21448 100% cotton | Dip | 1 | 5.48E+02 | 3.26 | 99.95% |
| | | 4 | 1.00E+02 | 4.27 | 99.99% |
| | | 24 | 6.52E+02 | 3.88 | 99.99% |
| | Spray | 1 | 4.47E+02 | 3.35 | 99.96% |
| | | 4 | 1.00E+02 | 4.27 | 99.99% |
| | | 24 | 1.00E+02 | 4.70 | 99.998% |

The results indicate potent residual antimicrobial efficacy on the Caring® PRM21448 100% cotton substrate, with the results somewhat better for swatches treated by the spray application method rather than the dip application method. These results demonstrate that cotton gauze treated with a solution of 3-aminopropyltrimethoxysilane and triethanolamine will find use as an antimicrobial wound dressing capable of mitigating the colonization of *Staph.* organisms potentially present on or in the wound situs.

Example 5

Cellulosic Dry Wiper/2030-2 and 2015

As a test substrate, a 2"×2" (4 sq. in.) sample of WypAll® L40 wiper, folded to total 4-ply was used. Only the dip coating procedure was used for this substrate due to its high capacity for liquid absorption. For the dip procedure, 5 mL of either the 2030-2 or 2015 formulations as indicated were used to saturate each cellulosic wiper test substrate swatch. The test substrates were deemed to be thoroughly dry prior to antimicrobial testing.

For this example, the Sanitization Test—Version 1 was used as described above, with *S. epidermidis* 12228 as the test organism. TABLE 14 sets forth the results from inoculating the dry test substrates with *S. epidermidis* 12228, (resident times=0, 1 hr., 4 hr., and 24 hr., respectively). Log and percent reduction were compared to time control group (uncoated test substrate swatches). Two replicates (N=2) swatches were used for both the uncoated and coated groups. The detection limit was 1 bacterium in 100 mL neutralizer broth=100 CFU/carrier.

TABLE 14

Time-Kill Study-*S. epidermidis* 12228-Time = 0, 1, 4, 24 hr. contact time

| Sample | Application Method | Contact Time (hr) | Mean Count (CFU/Carrier) | $Log_{10}$ Reduction | Percent Reduction |
|---|---|---|---|---|---|
| Uncoated WypAll ® L40 cellulose wiper | N/A | 0 | 1.56E+06 | N/A | |
| | | 1 | 1.19E+06 | N/A | |
| | | 4 | 8.87E+05 | N/A | |
| | | 24 | 5.00E+06 | N/A | |
| 2030-2 coated WypAll ® L40 cellulose wiper | Dip | 1 | 1.00E+02 | 4.08 | 99.99% |
| | | 4 | 1.00E+02 | 3.95 | 99.989% |
| | | 24 | 1.00E+02 | 4.70 | 99.998% |
| 2015 coated WypAll ® L40 cellulose wiper | | 1 | 1.09E+03 | 3.04 | 99.91% |
| | | 4 | 1.00E+02 | 3.95 | 99.99% |
| | | 24 | 1.00E+02 | 4.70 | 99.998% |

These results demonstrate that cellulosic dry wipers previously treated with either APTES/TEA (2030-2) or DMOD/CPTMS/TEA (2015) and then dried possess residual antimicrobial efficacy. The log kill numbers are remarkable and unexpected given the unconventional application of APTES as an antimicrobial active and the weak bacteriostatic activity typical of DMOD. These results show that a dry cellulosic wiper can be treated to retain residual antimicrobial efficacy, making the wipers useful for biohazard cleanup wherein organisms present in the bodily fluid and absorbed into the wiper during cleaning, should not be capable of multiplying to pathogenic levels within the wiper prior to the used wiper being incinerated.

Example 6

Consumer and Medical Professional Spray Product

A composition comprising the 2030-1 formulation, the 2030-2 formulation, or the 2015 formulation as disclosed herein, or formula modifications therefrom, can be packaged as an mixture with a propellant (e.g., liquefied gas e.g., propane, isobutene, etc.) in a standard aerosol can (e.g., a steel can with a crimped-on valve cup and actuator) or packaged in an extruded aluminum "bag-on-valve" system with $CO_2$ or $N_2$ used between the can and the bag to pressurize the bag. The latter packaging is available from Aurena Laboratories, Karlstad, Sweden, amongst other suppliers. The product provides a convenient way for consumers and healthcare professionals to treat bandaging, wraps, casts, compression sleeves and the like prior to placement on patients, or to treat the dressing and the skin areas around the dressing after the dressing is placed on the patient. The "bag-on-valve" packaging system allows for spraying at all angles, such as with the can held upside down, so as to provide for spraying around a patients limb, into the inside cavity of a compression sleeve prior to placement on a patient, and like applications.

Example 7

Triage Field Dressing

A composition comprising an aqueous solution of at least one organosilane of formula $(R^1O)_3Si$—$R^2$—Z, wherein each $R^1$ is independently H, alkyl, substituted alkyl, aryl, or substituted aryl, $R^2$ is a bivalent linker, and Z is a nucleophile, a leaving group or a quaternary nitrogen substituent, is soaked into 10"×30" multi-trauma dressing and air dried. Following drying, the treated dressing may be packaged in sterile packaging until use. In a triage setting, the multi-trauma dressing is opened to the size appropriate for the particular wound, applied to the wound with pressure, and then wrapped and secured with gauze bandage and clips. While the victim is being transported to a medical care facility, the antimicrobial organosilane dissolves from the multi-trauma dressing into the wound exudate and blood and into the surrounding traumatized tissue to bathe the wound in antimicrobial actives while the patient is being transported to a medical facility. In this way, infections are mitigated in the time between the trauma and the medical care at a hospital.

Antimicrobial coating compositions, methods for applying antimicrobial coating compositions to medical dressings, including gauzes of various types and dry wiper substrates, and residual antimicrobial coatings that provide prolonged antimicrobial efficacy are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for a composition or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

We claim:

1. A dry medical dressing comprising:
a nonwoven or woven substrate; and
an antimicrobial coating dried thereon, the antimicrobial coating formed from an aqueous antimicrobial coating composition consisting essentially of a mixture of 0.75 wt. % octadecyldimethyl-(3-trimethoxysilylpropyl) ammonium chloride, 0.12 wt. % 3-chloropropyltrimethoxysilane, 0.045 wt. % triethanolamine and remainder water;
wherein the dry medical dressing exhibits a >3 $\log_{10}$ reduction of *S. epidermidis* 4-hours after inoculation of *S. epidermidis* thereon.

2. The dry medical dressing of claim 1, wherein the substrate comprises a cellulose wiper.

3. The dry medical dressing of claim 1, wherein the substrate comprises polyester gauze.

4. A method of producing a dry medical dressing, the method comprising:
saturating a medical dressing with an aqueous composition consisting essentially of a mixture of 0.75 wt. % octadecyldimethyl-(3-trimethoxysilylpropyl) ammonium chloride, 0.12 wt. % 3-chloropropyltrimethoxysilane, 0.045 wt. % triethanolamine, remainder water; and
drying the medical dressing to produce the dry medical dressing,
wherein the dry medical dressing exhibits residual antimicrobial efficacy against at least one of *E. coli*, *S. aureus*, or *S. epidermidis*.

5. The method of claim 4, wherein the drying comprises ambient, passive drying to provide the dry medical dressing perceived as dry to the touch.

6. The method of claim 4, wherein the medical dressing is selected from the group consisting of adhesive bandages, gauze rolls, gauze pads, wraps, sponge material, breathable films, patient gowns, examination gowns, surgical gowns, and disposable dry wiper substrates.

7. The method of claim 6, wherein the medical dressing comprises a cellulose wiper.

8. The method of claim 6, wherein the medical dressing comprises polyester gauze.

* * * * *